(12) United States Patent
Officier

(10) Patent No.: US 9,510,971 B2
(45) Date of Patent: Dec. 6, 2016

(54) FORCED AIR WARMER

(75) Inventor: Arthur Everardus Officier, Epe (NL)

(73) Assignee: THE SURGICAL COMPANY INTERNATIONAL B.V., Amersfoort (NL)

( * ) Notice: Subject to any disclaimer, the term of this patent is extended or adjusted under 35 U.S.C. 154(b) by 1157 days.

(21) Appl. No.: 13/568,608

(22) Filed: Aug. 7, 2012

(65) Prior Publication Data

US 2014/0046412 A1 Feb. 13, 2014

(51) Int. Cl.
*A61F 7/00* (2006.01)

(52) U.S. Cl.
CPC .............. *A61F 7/0085* (2013.01); *A61F 7/007* (2013.01); *A61F 7/0097* (2013.01); *A61F 2007/006* (2013.01); *A61F 2007/0072* (2013.01); *A61F 2007/0086* (2013.01); *A61F 2007/0096* (2013.01)

(58) Field of Classification Search
CPC ........... A61F 7/0085; A61F 2007/006; A61F 2007/0086; A61F 2007/0096
See application file for complete search history.

(56) References Cited

U.S. PATENT DOCUMENTS

| 6,126,681 A | 10/2000 | Van Duren et al. |
| 2008/0159354 A1* | 7/2008 | Fleming ............... G01K 13/028 374/138 |
| 2008/0228247 A1* | 9/2008 | Fung ....................... A61F 7/007 607/107 |

OTHER PUBLICATIONS

"Mistral-Air Plus Forced Air Warming" Technical Manual, TSCI, The Surgical Company International B.V., The Netherlands, 2009, (48 pgs.).

* cited by examiner

*Primary Examiner* — Kaitlyn Smith
(74) *Attorney, Agent, or Firm* — Nixon & Vanderhye P.C.

(57) ABSTRACT

The invention provides a forced air warmer comprising: a chamber having an outlet port; an air heater arranged to heat air within the chamber; an air propagator arranged to propagate heated air from the chamber along a heated air flow path passing through the port; and a temperature sensor provided in the heated air flow path to measure the temperature of heated air propagated along the heated air flow path. The forced air warmer further comprises an air flow conditioner in the heated air flow path downstream of the temperature sensor, the air flow conditioner being arranged to condition air flow at the temperature sensor so as to improve the reliability of temperature measurements made by the temperature sensor. The forced air warmer may be used to supply heated air to an air warming blanket for regulating the temperature of a patient.

20 Claims, 21 Drawing Sheets

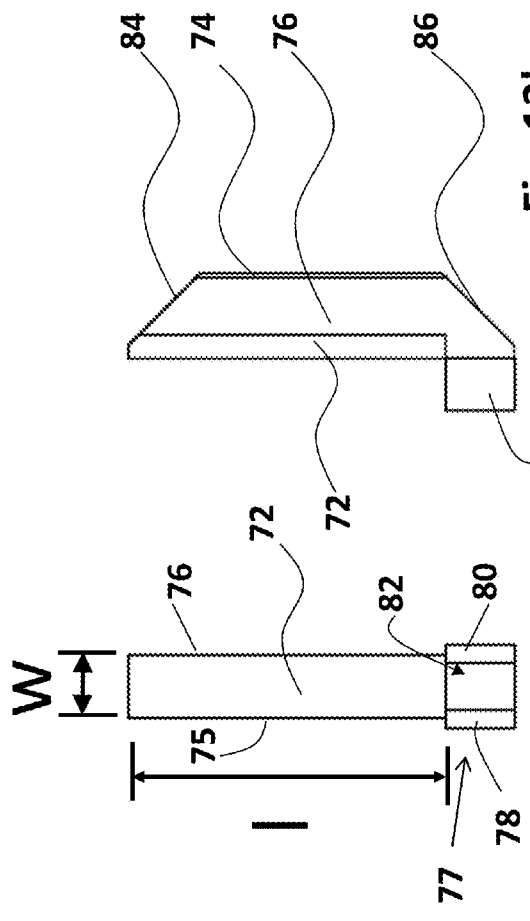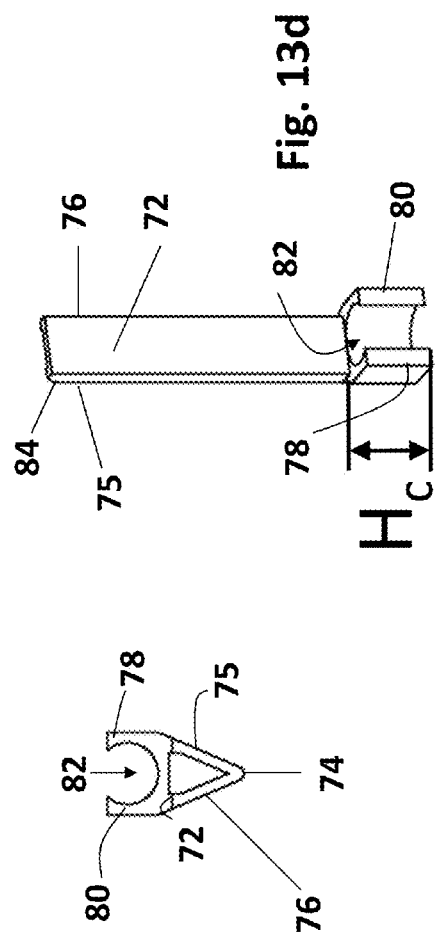

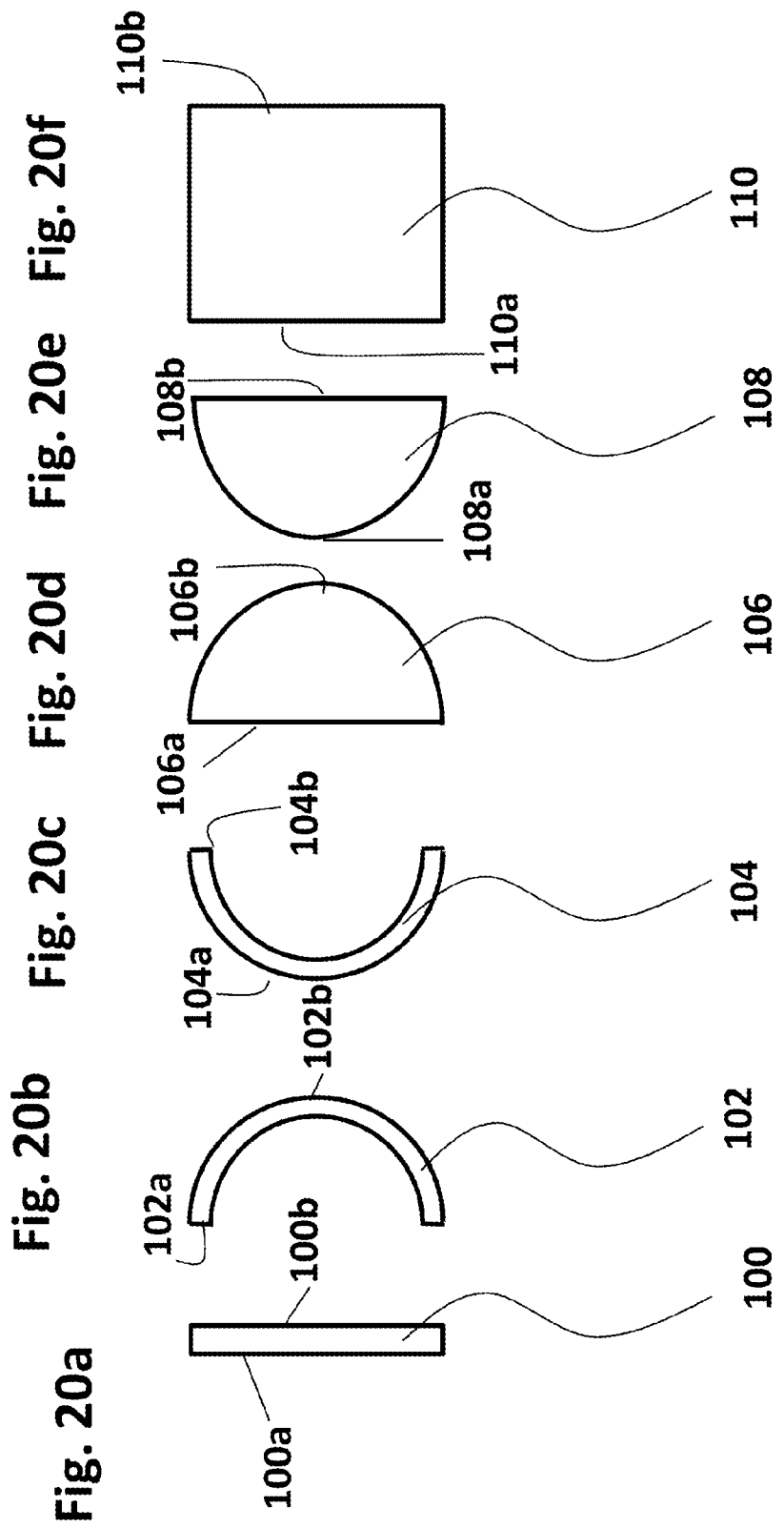

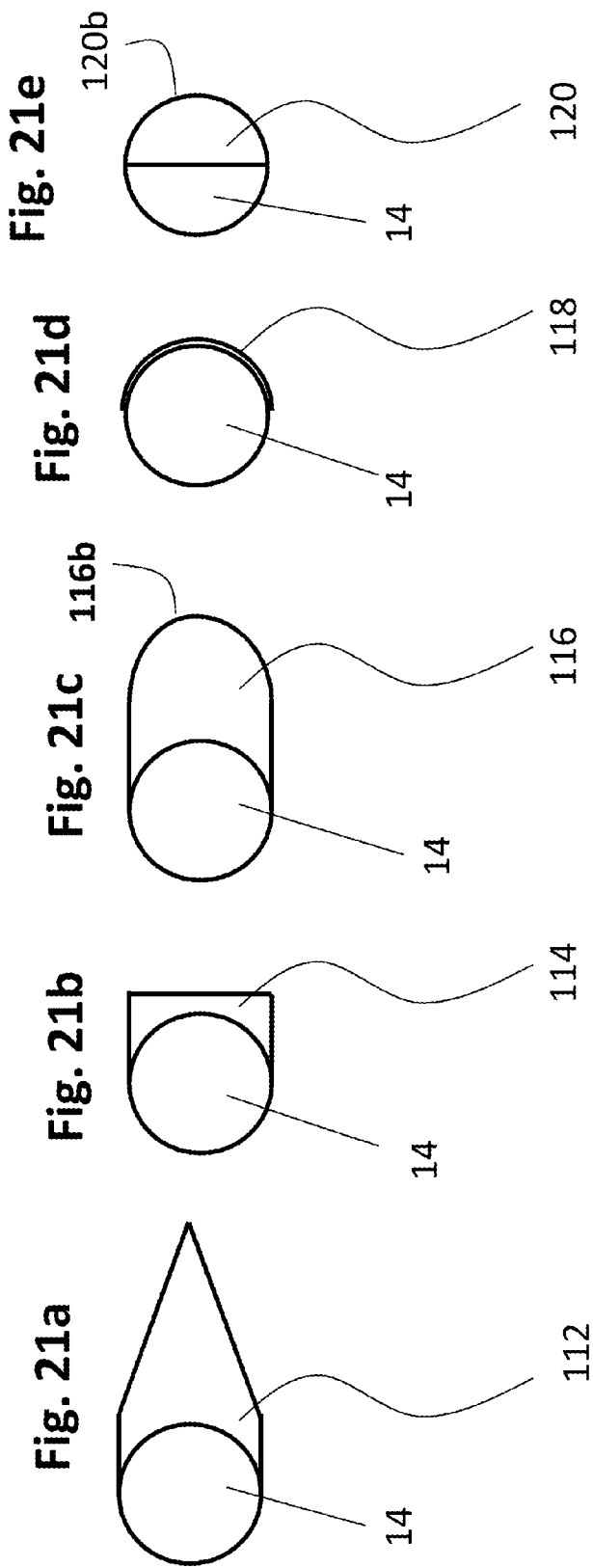

FORCED AIR WARMER

FIELD OF THE INVENTION

The invention relates to a forced air warmer, a method of measuring the temperature of heated air in a forced air warmer and an air flow conditioner for use in a forced air warmer.

BACKGROUND TO THE INVENTION

Forced air warmers may be used in both hypo- and hyperthermia treatments to help to regulate the temperature of a patient. These devices typically comprise an air heating device provided inside a chamber, a flexible hose in air communication with the chamber and a blower arranged to transport heated air from the chamber through the hose into a forced air warming blanket. Typically, the forced air warming blanket comprises an air permeable surface facing the patient.

A key requirement for forced air warmers is that the temperature of the air being provided to the forced air warming blanket can be measured reliably and accurately. The temperature of the heated air would ideally be measured at the forced air warming blanket. However, this is not typically possible. Accordingly, the temperature of the heated air must typically be measured elsewhere.

One possible solution is to measure the temperature of the heated air at an outlet of the chamber. However, temperature measurements made at the outlet of the chamber have been found to be subject to variable errors, and are therefore unreliable. Another possible solution is to measure the temperature of the heated air at an outlet of the flexible hose. However, this requires the hose to include a temperature sensor and wiring which is expensive and is subject to breakage with repeated use of the hose.

Accordingly, the invention addresses the technical problem of how to reliably, accurately and inexpensively measure the temperature of heated air provided by a forced air warmer.

SUMMARY OF THE INVENTION

A first aspect of the invention provides a forced air warmer comprising: a chamber having an outlet port; an air heater arranged to heat air within the chamber; an air propagator arranged to propagate heated air from the chamber along a heated air flow path passing through the port; and a temperature sensor provided in the heated air flow path to measure the temperature of heated air propagated along the heated air flow path, characterised by an air flow conditioner in the heated air flow path downstream of the temperature sensor, the air flow conditioner being arranged to condition air flow at the temperature sensor so as to improve the reliability of temperature measurements made by the temperature sensor.

Positioning a temperature sensor in the heated air flow path destabilises the flow of heated air through the port downstream of the temperature sensor. This unstable air flow can cause one or more vortices to be generated. The number, magnitude and orientation of these vortices are dependent on the velocity of the air flow at the temperature sensor and on backstream conditions at the temperature sensor. Because the vortices are variable in number, magnitude and orientation, varying amounts of air are circulated back upstream onto the temperature sensor by the vortices. This causes variable errors to be incurred in the temperature measurements made by the temperature sensor which can be difficult (if not impossible) to account for by calibration. By conditioning the air flow downstream of the temperature sensor, the air flow at the temperature sensor can be stabilised, thus improving the reliability of the temperature measurements made by the temperature sensor (relative to the situation when the air flow conditioner is removed).

Preferably, the port has a connector which is couplable to a flexible hose, either directly or via another connector provided on the flexible hose.

When a flexible hose is coupled to the port (typically via the connector), air heated by the air heater is propagated through the port into the hose by the air propagator. The flexible hose affects backstream conditions at the temperature sensor. For example, it has been found that, in the absence of the flow conditioner, the bending profile of the flexible hose affects the number, magnitude and orientation of the vortices generated downstream of the temperature sensor. Accordingly, in the absence of the flow conditioner, the errors are incurred in the temperature measurements made by the temperature sensor are variable with changes in the bending profile of the flexible hose. By conditioning the air flow downstream of the temperature sensor, the air flow at the temperature sensor can be stabilised to reduce or even prevent the variable upstream flow of recirculated air onto the temperature sensor caused by the vortices affected by changes in the bending profile of the hose, thus improving the reliability of the temperature measurements made by the temperature sensor (relative to the situation when the air flow conditioner is removed).

Any restrictions in the flexible hose can also affect the backstream conditions at the temperature sensor. For example, restrictions can affect the back pressure exerted on the flow of propagated air through the hose. This can also affect the number, magnitude and orientation of the vortices generated downstream of the temperature sensor. Again, by conditioning the air flow downstream of the temperature sensor, the air flow at the temperature sensor can be stabilised, thus improving the reliability of the temperature measurements made by the temperature sensor (relative to the situation when the air flow conditioner is removed).

Typically, the forced air warmer comprises a controller in electronic communication with both the temperature sensor and the air heater (and optionally the air propagator), the controller being configured to regulate the temperature of air heated by the air heater in response to temperature measurement data fed back to the controller from the temperature sensor. The controller may comprise, for example, an electronic processor or microcontroller. Errors in the temperature measurements made by the temperature sensors thus affect the temperature of heated air provided by the forced air warmer.

Typically the temperature sensor is positioned in, or adjacent to, the outlet port of the chamber.

Typically, the air flow conditioner is positioned adjacent to the temperature sensor.

Although the air flow conditioner may be provided in contact with the temperature sensor, preferably the air flow conditioner is spaced apart from the temperature sensor. By spacing the flow conditioner from the temperature sensor, the temperature reading of the temperature sensor is not adversely influenced by the additional mass and heat absorption characteristics of the flow conditioner. Preferably, the air flow conditioner is not in thermal contact with the temperature sensor. Preferably, the air flow conditioner is not in direct thermal communication with the temperature sensor.

It will be understood that the temperature sensor provided in the heated air flow path may form part of a temperature sensing system. For example, the temperature sensor provided in the heated air flow path may be a thermocouple which may (and would typically) be connected to a measuring device or a processor (e.g. microcontroller or microprocessor) outside of the chamber.

By the heated air flow path we refer to the principle direction of heated air propagation from the air propagator through the port.

Typically, the air propagator is an air blower or fan.

In some embodiments, the air flow conditioner may be arranged to condition the flow by acting as a barrier which inhibits an upstream flow of air onto the temperature sensor. By inhibiting the upstream flow of air onto the temperature sensor, the reliability of temperature measurements made by the temperature sensor can be improved.

In one embodiment, the air flow conditioner comprises a plate.

It will be understood that the plate may have any suitable profile. However, the profile of the plate may be selected in dependence on the shape of the temperature sensor. In one embodiment, the temperature sensor has an elongate profile. In this case, the plate preferably has an elongate profile. For example, the plate may have a rectangular profile in a plane perpendicular to the heated air flow path.

Typically, the plate is substantially flat.

Preferably, the plate comprises a blocking surface which is arranged to inhibit the said upstream flow of air onto the temperature sensor.

Typically, the blocking surface is substantially planar.

Preferably, the blocking surface lies on a plane which is substantially perpendicular to the heated air flow path.

The air flow conditioner may have a profile to which air propagated along the heated air flow path conforms. The shape of the profile affects the nature of the air flow downstream of the temperature sensor. Accordingly, the profile is preferably shaped to delay or prevent flow separation downstream of the temperature sensor. The profile may also have an aerodynamic shape to minimise the drag caused to the air flow by the air flow conditioner.

In some embodiments, the air flow conditioner further comprises a leading edge and a trailing edge, the leading edge being positioned upstream of a trailing edge, wherein the profile of the air flow conditioner to which the air propagated along the heated air flow path conforms has a width perpendicular to the heated air flow path, the width varying in magnitude between the leading and trailing edges to condition the flow.

It will be understood that the width of the air flow conditioner need not vary constantly or consistently between the leading and trailing edges. In some embodiments, the width of the air flow conditioner may vary in magnitude for only part of the distance between the leading and trailing edges.

By varying the width of the profile, the air flow conditioner can be configured to condition the air flow at the temperature sensor in a desired way (e.g. to prevent or delay flow separation). In addition, the profile can be provided with an aerodynamic shape to minimise drag.

Preferably, the air flow conditioner is arranged such that air flows along at least two opposing sides of the profile. Preferably two of the at least two opposing sides are separated by the width of the air flow conditioner.

The width of the air flow conditioner may taper down in magnitude between the leading and trailing edges.

Again it will be understood that the width of the air flow conditioner need not taper down in magnitude constantly or consistently between the leading and trailing edges.

In one embodiment, the width of the air flow conditioner tapers down in magnitude to form a wedge shaped profile along the heated air flow path. In this case, the width of the air flow conditioner preferably tapers down in magnitude constantly and/or consistently between the leading and trailing edges.

In one embodiment, the width of the air flow conditioner tapers to form an aerofoil shaped profile along the heated air flow path. In this case, the width of the air flow conditioner may increase initially from the leading edge along the heated air flow path before tapering down in magnitude towards the trailing edge.

Both the wedge and aerofoil shaped profiles are aerodynamic, such that the drag caused by the air flow conditioner is minimal.

Preferably, the profile of the air flow conditioner to which the air propagated along the heated air flow path conforms has a length perpendicular to the heated air flow path, the length varying in magnitude between the leading and trailing edges.

The length of the air flow conditioner does not necessarily vary constantly or continuously between the leading and trailing edges. The length of the air flow conditioner may not vary constantly and/or continuously between the leading and trailing edges. Alternatively the length of the air flow conditioner may vary constantly and/or continuously between the leading edge and the trailing edge.

By varying the length of the air flow conditioner between the leading and trailing edges, one or more angled surfaces can be provided between portions of the air flow conditioner having different lengths. If a flexible hose is coupled to the port, these angled surfaces help to prevent rupture of the hose when the hose bends near the port.

Typically, an average length of the air flow conditioner is of greater magnitude than an average width of the air flow conditioner.

Although the angled surfaces between portions of the air flow conditioner having different lengths may be used to condition the air flow at the temperature sensor, the angled surfaces between portions of the air flow conditioner having different lengths may not be used to condition the air flow at the temperature sensor.

Preferably, the air flow conditioner at least partially covers the temperature sensor when viewed in an upstream direction of the heated air flow path from downstream of the air flow conditioner.

By at least partially covering the temperature sensor with the air flow conditioner when viewed in the upstream direction of the heated air flow path from downstream of the air flow conditioner, it can be ensured that at least some of the air flow disturbed by the temperature sensor is caused to conform to the profile of the air flow conditioner.

In one embodiment, the air flow conditioner covers the entire length of the temperature sensor when viewed in the upstream direction of the heated air flow path from downstream of the air flow conditioner, but covers only part of the width of the temperature sensor when viewed in this direction.

Preferably the air flow conditioner covers the entire temperature sensor (i.e. both the entire length and the entire width of the temperature sensor) when viewed along the heated air flow path in the upstream direction of the heated air flow path from downstream of the air flow conditioner such that substantially all of the air flow disturbed by the temperature sensor is caused to conform to the profile of the air flow conditioner.

Preferably, the temperature sensor extends from a first internal wall of the port towards a second internal wall of the port opposite the first internal wall to a first extent and the air flow conditioner extends from the first internal wall to the second internal wall to a second extent, the second extent being greater than the first extent.

The first and second extents are typically the maximum extents by which the temperature sensor and air flow conditioner extend from the first internal wall towards the second internal wall.

By making the second extent greater than or equal to the first extent, the air flow conditioner can be made to cover the temperature sensor in at least one dimension when viewed along the heated air flow path.

Preferably, the second extent is substantially equal to the shortest distance between the first and second internal walls. In this case, the air flow conditioner extends from the first internal wall to the second internal wall, which optimises the quantity of air flow conditioned by the air flow conditioner.

A flexible hose may be provided separately from the forced air warmer. Additionally or alternatively, a flexible hose may be coupled (typically detachably) to the outlet port of the chamber.

Typically, the hose is connectable, or connected, to a forced air warming blanket.

Thus, one possible use for the forced air warmer is to provide heated air to an air warming blanket for regulating the temperature of a (typically human) medical patient (e.g. during surgery or during a medical procedure). In this case, the temperature of the heated air provided by the forced air warmer determines whether and to what extent a medical patient is heated or cooled by the air warming blanket. For example, if the temperature of the heated air provided by the forced air warmer is >37° C., the air provided by the forced air warmer may be used to heat a patient but if the temperature of heated air provided by the forced air warmer is <37° C., the air provided by the forced air warmer may be used to cool a patient. In the absence of the flow conditioner, it has been found that errors of between 1° C. and 4° C. are incurred in the temperature measurements made by the temperature sensor. This is because, without the flow conditioner, the vortices generated downstream of the temperature sensor affect both the velocity of the local air flow at the temperature sensor and the surface area of the temperature sensor which is in contact with the air flow. Thus, because the bending profile of the hose is typically variable in use, both the velocity of the local air flow at the temperature sensor and the surface area of the temperature sensor which is in contact with the local air flow are also variable. These result in a greater rate of heat transfer from the local air flow to the temperature sensor. This greater rate of heat transfer to the temperature sensor causes a falsely high temperature measurement being made by the temperature sensor. Consequently, the temperature measurements fed back to the controller from the temperature sensor are greater than the actual temperature of the air heated by the air heater. As a result, the controller may incorrectly decrease the amount of heat energy supplied by the air heater and the heated air supplied by the forced air warmer to the air warming blanket may thus be underheated. Ultimately, this may cause the patient to be underheated by the air warming blanket, or even cause the patient to be cooled when heating was intended. The improvement in reliability provided by the presence of the air flow conditioner typically improves the accuracy of the temperature measurements made by the temperature sensor such that the air provided by the forced air warmer more reliably heats and cools a patient as intended in use.

Although the air flow conditioner may be bonded or fastened to the temperature sensor, the forced air warmer typically comprises a clamp configured to connect the air flow conditioner to the temperature sensor. Such a clamp provides a convenient means by which the air flow conditioner can be mounted in the heated air flow path.

Preferably, the clamp is configured to space the air flow conditioner from the temperature sensor. By configuring the clamp appropriately, the clamp can ensure that a desired spacing is provided between the temperature sensor and the air flow conditioner.

Preferably, the clamp thermally insulates the air flow conditioner from the temperature sensor. This ensures that the air flow conditioner does not affect the temperature measurements made by the temperature sensor.

The clamp may be integrally formed with the air flow conditioner. Alternatively, the clamp may be formed separately from the air flow conditioner, and subsequently bonded or fastened to the air flow conditioner.

Typically, the temperature sensor has a rounded perimeter. Preferably, the temperature sensor is substantially cylindrical.

Rounded perimeters, although typical of temperature sensors, are prone to cause unstable air flows downstream. Accordingly, it is particularly beneficial to provide an air flow conditioner downstream of the temperature sensor as defined by the first aspect of the invention when the temperature sensor has a rounded perimeter.

A second aspect of the invention provides a method of measuring the temperature of heated air in a forced air warmer, the method comprising:
  a. heating air within a chamber;
  b. propagating the heated air from the chamber along a heated air flow path passing through an outlet port of the chamber; and
  c. measuring the temperature of the propagated heated air at the port using a temperature sensor provided in the heated air flow path,
  characterised in that the method further comprises conditioning air flow at the temperature sensor using an air flow conditioner positioned in the heated air flow path downstream of the temperature sensor so as to improve the reliability of the temperature measurements made by the temperature sensor.

By "at the port", we mean either in the port or adjacent to the port.

A third aspect of the invention provides an air flow conditioner for use in the forced air warmer according to the first aspect of the invention.

A fourth aspect of the invention provides an air flow conditioner comprising: a leading edge; a trailing edge; and a profile extending between the leading and trailing edges, the profile having a width extending perpendicularly to a line extending perpendicularly between the leading and trailing edges, wherein the width of the profile varies between the leading and trailing edges.

The width of the profile preferably varies between the leading and trailing edges to form an aerodynamic shape.

In some embodiments, the width of the air flow conditioner decreases between the leading and trailing edges.

In one embodiment, the width of the air flow conditioner decreases between the leading and trailing edges to form a wedge shaped profile.

In one embodiment, the width of the air flow conditioner varies between the leading and trailing edges to form an aerofoil shaped profile.

Typically, the air flow conditioner has a length which extends perpendicularly to the width and to the line extending perpendicularly between the leading and trailing edges. In one embodiment, the length of the air flow conditioner varies (but not necessarily constantly or continuously) between the leading and trailing edges.

The length of the air flow conditioner is typically of greater magnitude than the width of the air flow conditioner.

A fifth aspect of the invention provides a method of regulating the temperature of heated air provided by a forced air warmer, the method comprising: heating air within a chamber of the forced air warmer; propagating the heated air from the chamber along a heated air flow path passing through an outlet port of the chamber; measuring the temperature of the propagated heated air at the port using a temperature sensor provided in the heated air flow path; conditioning air flow at the temperature sensor using an air flow conditioner positioned in the heated air flow path downstream of the temperature sensor; and regulating the heating applied to air within the chamber in dependence on the temperature measurements made by the temperature sensor.

Typically, the heating applied to the air within the chamber is regulated by a controller in electronic communication with an air heater used to heat the air within the chamber.

The preferred and optional features discussed above are preferred and optional features of each aspect of the invention to which they are applicable. For the avoidance of doubt, the preferred and optional features of the first aspect of the invention correspond are preferred and optional features of the second, third, fourth and fifth aspects of the invention, where applicable.

DESCRIPTION OF THE DRAWINGS

An example embodiment of the present invention will now be illustrated with reference to the following Figures in which:

FIGS. 13a-13d provide various views of the air flow conditioner of FIG. 12;

FIGS. 20a-20f show six alternative profiles for the air flow conditioner; and

FIGS. 21a-21e show five alternative temperature sensors each having a different air flow conditioner which is integrally formed with the temperature sensor or bonded or fastened thereto.

DETAILED DESCRIPTION OF AN EXAMPLE EMBODIMENT

Figure 1:
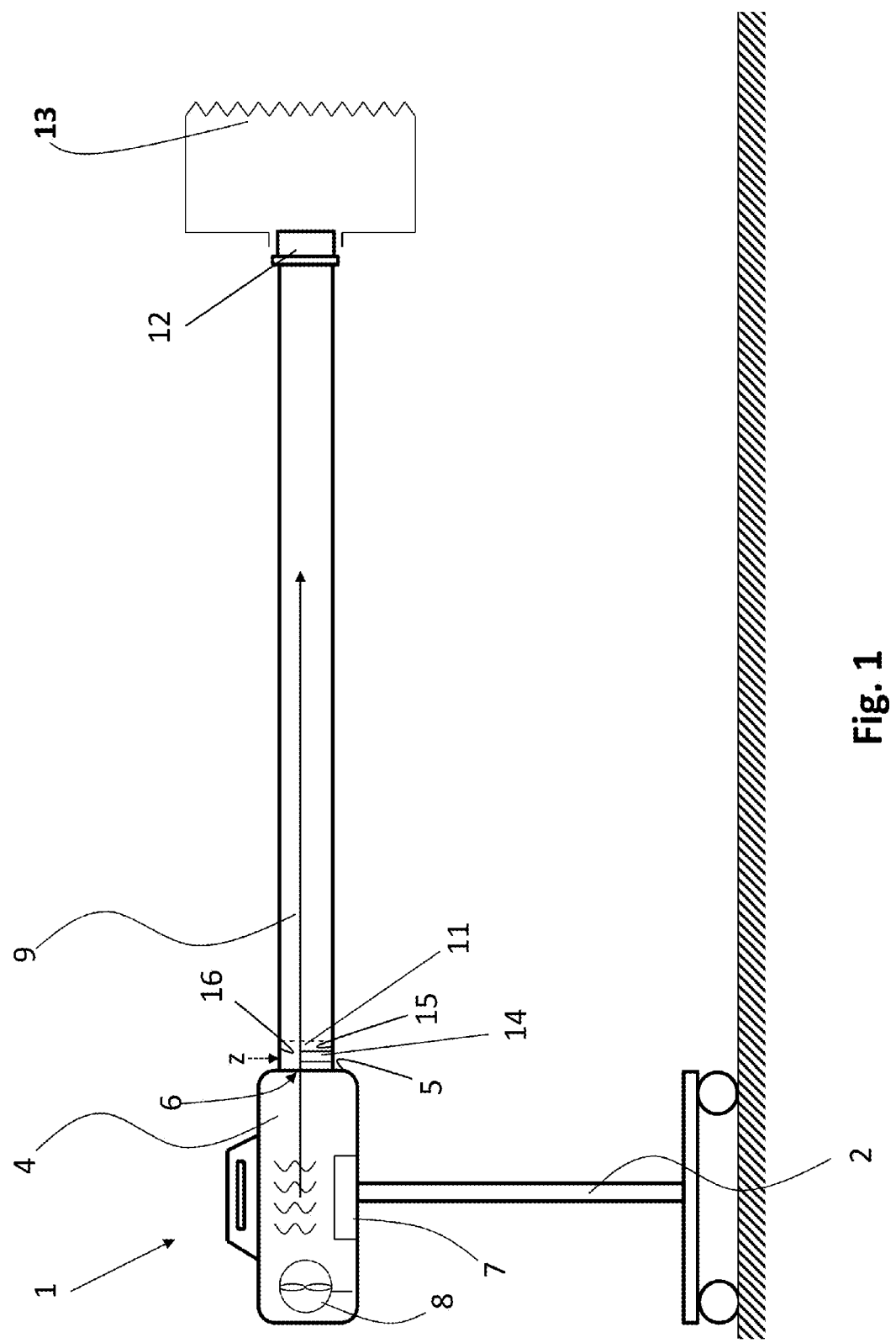
FIG. 1 is a schematic diagram of a forced air warmer mounted on a trolley connected via a flexible hose to a forced air warming blanket.

FIG. 1 is a schematic diagram of a forced air warmer 1 mounted on a trolley 2, the forced air warmer 1 comprising: a chamber 4 having a side wall 5 with an outlet port 6 through which air can exit the chamber 4; an air heater 7 and an air blower 8 housed within the chamber 4; and a flexible hose 9 demountably coupled to the outlet port 6 such that the hose 9 is in fluid communication with the chamber 4.

The air heater 7 is arranged to heat air within the chamber 4 and the air blower 8 is arranged to propagate heated air from the chamber 4 along a heated air flow path (indicated by an arrow in FIG. 1) passing through the outlet port 6 into the flexible hose 9. The flexible hose 9 comprises a proximal end 11 which is demountably coupled to a cylindrical connector 10 of the outlet port 6 which projects outwardly from the side wall 5 of the chamber 4 and surrounds an opening of the outlet port 6 (shown most clearly in FIG. 12). The flexible hose 9 further comprises a distal end 12 which is demountably coupled to a forced air warming blanket 13. The flexible hose 9 carries heated air between the forced air warmer 1 and the forced air warming blanket 13.

A temperature sensor 14, such as a thermocouple, thermistor, platinum resistance thermometer or semiconductor temperature sensor (or any other suitable temperature sensor), is provided in the heated air flow path in, or adjacent to, the outlet port 6 to monitor the temperature of heated air supplied to the flexible hose 9 which in turn provides an indication of the temperature of the heated air supplied to the forced air warming blanket 13 (although there will typically be some heat loss between the outlet port 6 of the forced air warmer 1 and the forced air warming blanket 13, and therefore calibration of the temperature sensor 14 is typically required to take this heat loss into account). The temperature sensor 14 extends from a first internal wall 15 of the port 6 towards a second internal wall 16 of the port 6 opposite the first internal wall 15. The internal walls 15, 16 may be part of the side wall 5 of the chamber 4 or side walls of the connector 10. The temperature sensor 14 typically forms part of a temperature measurement system. For example, the temperature measurement system may comprise a thermocouple electrically coupled to a measuring device provided outside of the chamber 4, wherein the temperature sensor 14 may be the portion of the thermocouple provided within the heated air flow path.

Typically, a controller is provided (external to the chamber 4) in electronic communication with both the temperature sensor 14 and the air heater 7 (and optionally the blower 8), the controller being configured to regulate the temperature of the air heated by air heater 7 using temperature measurements fed back to the controller by the temperature sensor 14. The controller may comprise, for example, an electronic processor.

Figure 2:
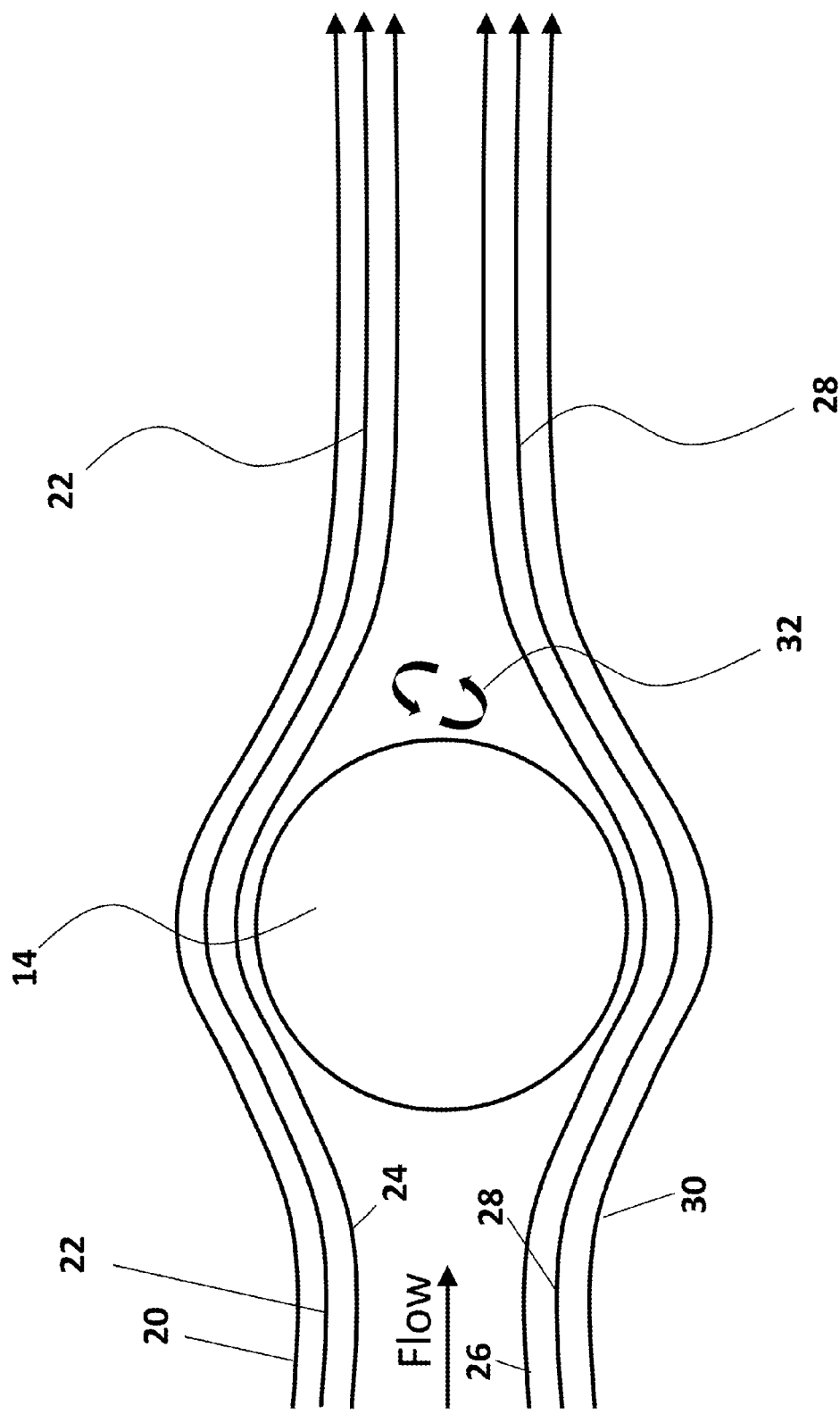
FIG. 2 is a schematic diagram illustrating idealised air flow lines around a temperature sensor provided in a heated air flow path of the forced air warmer of FIG. 1.

FIG. 2 is a schematic top down sectional view of the outlet port 6 of the chamber 4 and the proximal end 11 of the flexible hose 9 as viewed in the "Z" direction indicated in FIG. 1. The temperature sensor 14 has a rounded (typically cylindrical) profile when viewed in this direction. The flow of heated air propagated from the chamber 4 by the blower 8 through the port 6, as illustrated by flow lines 20-30, is disturbed by the presence of the temperature sensor 14 in the heated air flow path. Ideally, the air flow would remain attached downstream of the temperature sensor 14, or alternatively a constant wake 32 would be generated downstream of the temperature sensor 14. In either case, the temperature measurements of the heated air made by the temperature sensor 14 would typically be accurate due to the constant air flow conditions at the temperature sensor, although as indicated above calibration of the temperature sensor may be necessary to take into account heat losses in the hose 9 between the outlet port 6 of the chamber 4 and the forced air warming blanket 13. As shown in the arrangement of FIG. 1, the flexible hose 9 may be secured to follow a straight line path from the forced air warmer 1 to the forced air warming blanket 13, to help maintain constant flow conditions downstream of the temperature sensor 14.

Figure 3:
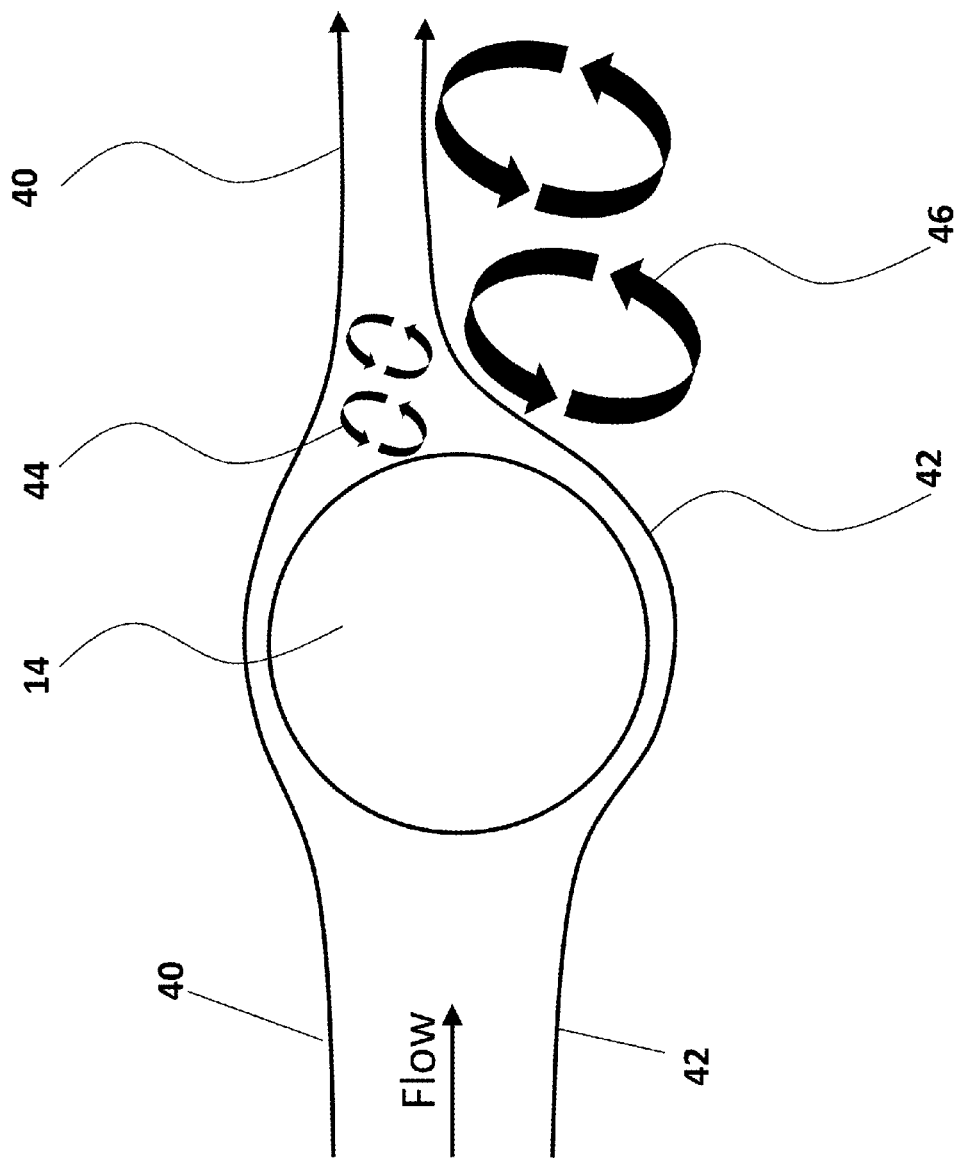
FIGS. 3 and 4 are schematic diagrams illustrating more typical air flow lines around the temperature sensor shown in FIGS. 1 and 2.
Figure 4:
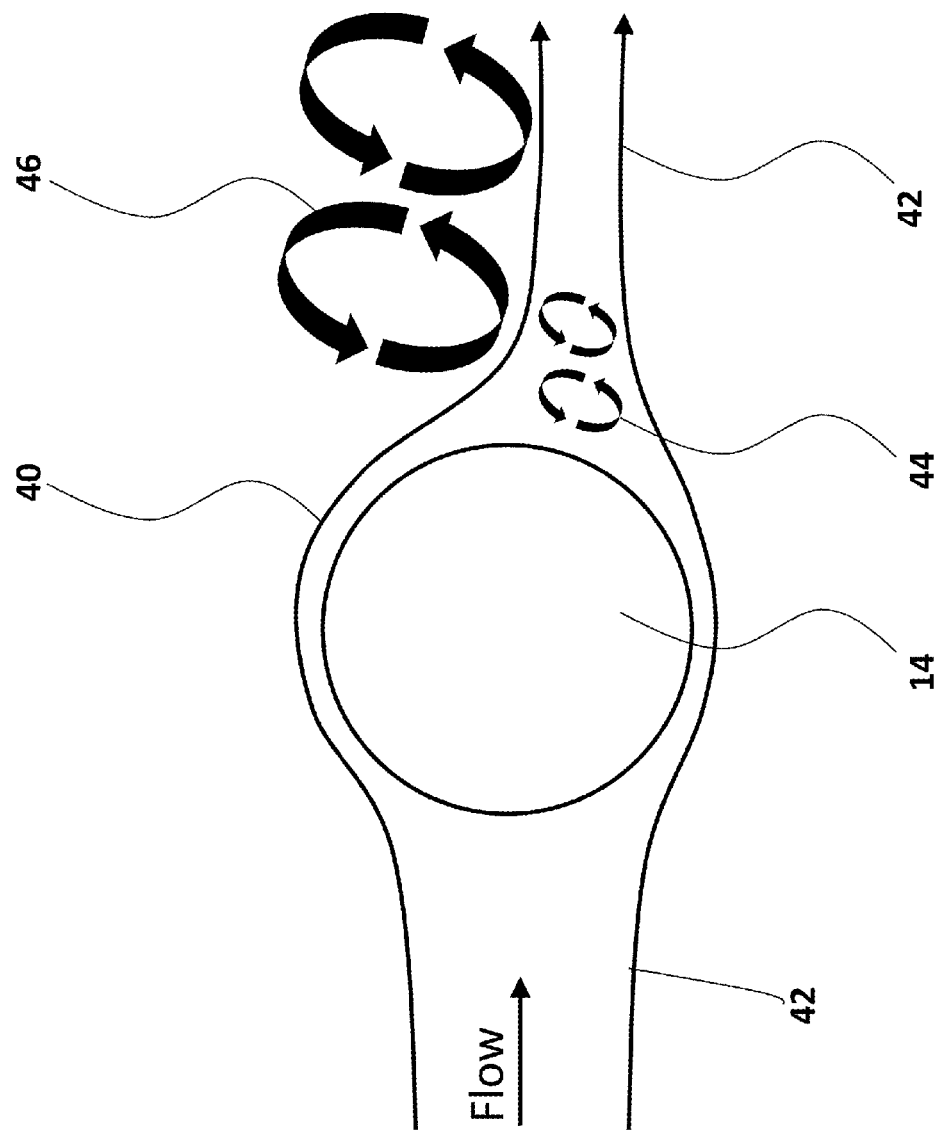

However, it has been found that the presence of the temperature sensor 14 typically causes the air flow to separate downstream of the temperature sensor 14. This is illustrated by FIGS. 3 and 4 which show more typical flow lines 40-42 around the temperature sensor 14, which separate to cause the generation of vortices 44, 46 which in turn cause air to flow back upstream onto the temperature sensor 14. The number, magnitude and orientation of vortices generated downstream of the temperature sensor are variable with the air flow velocity at the temperature sensor and with backstream conditions at the temperature sensor 14. This is illustrated by the change in position of the vortices 44, 46 between FIGS. 3 and 4. As a result of the number, magnitude and orientation of the vortices being variable over time, the local air flow velocity at the temperature sensor and the surface area of the temperature sensor in contact with the air flow also changes over time, causing a varying rate of heat transfer from the air flow to the sensor 14. Ultimately, this causes varying errors in the temperature measurements made by the temperature sensor 14 which cannot easily (if at all) be accounted for by calibration of the temperature sensor 14.

Figure 5:
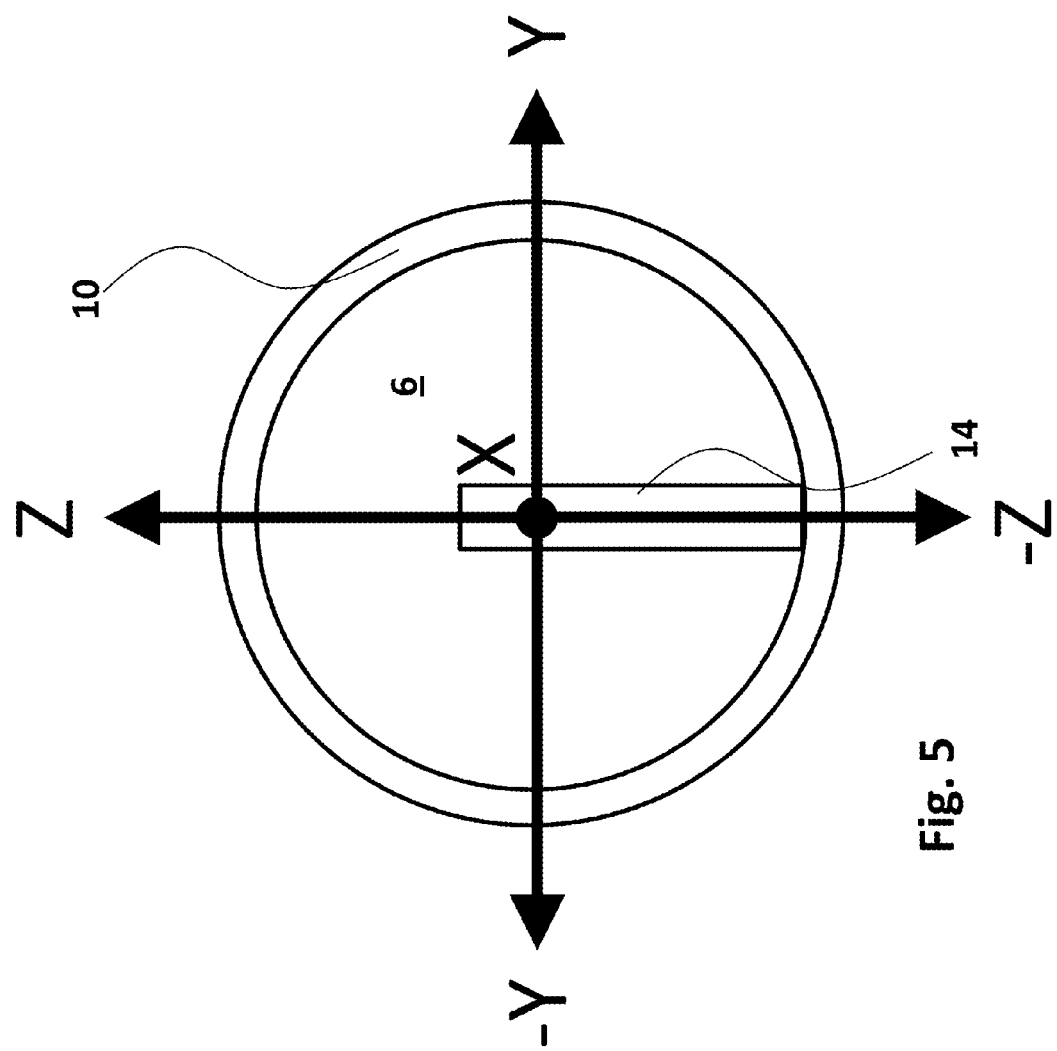
FIG. 5 is an end sectional view of an outlet port of the chamber of the forced air warmer of FIG. 1.

FIG. 5 is an end sectional view of the outlet port 6 of the chamber 4, also showing the temperature sensor 14. X, Y and Z directions are defined in FIG. 5, the X direction being defined along the heated air flow path, the Z direction being parallel to a longitudinal axis of the temperature sensor 14 (as indicated above and in FIG. 1) and the Y direction being perpendicular to the X and Z directions. The flexible hose 9 may be bent in either the Y or Z directions.

Figure 6:
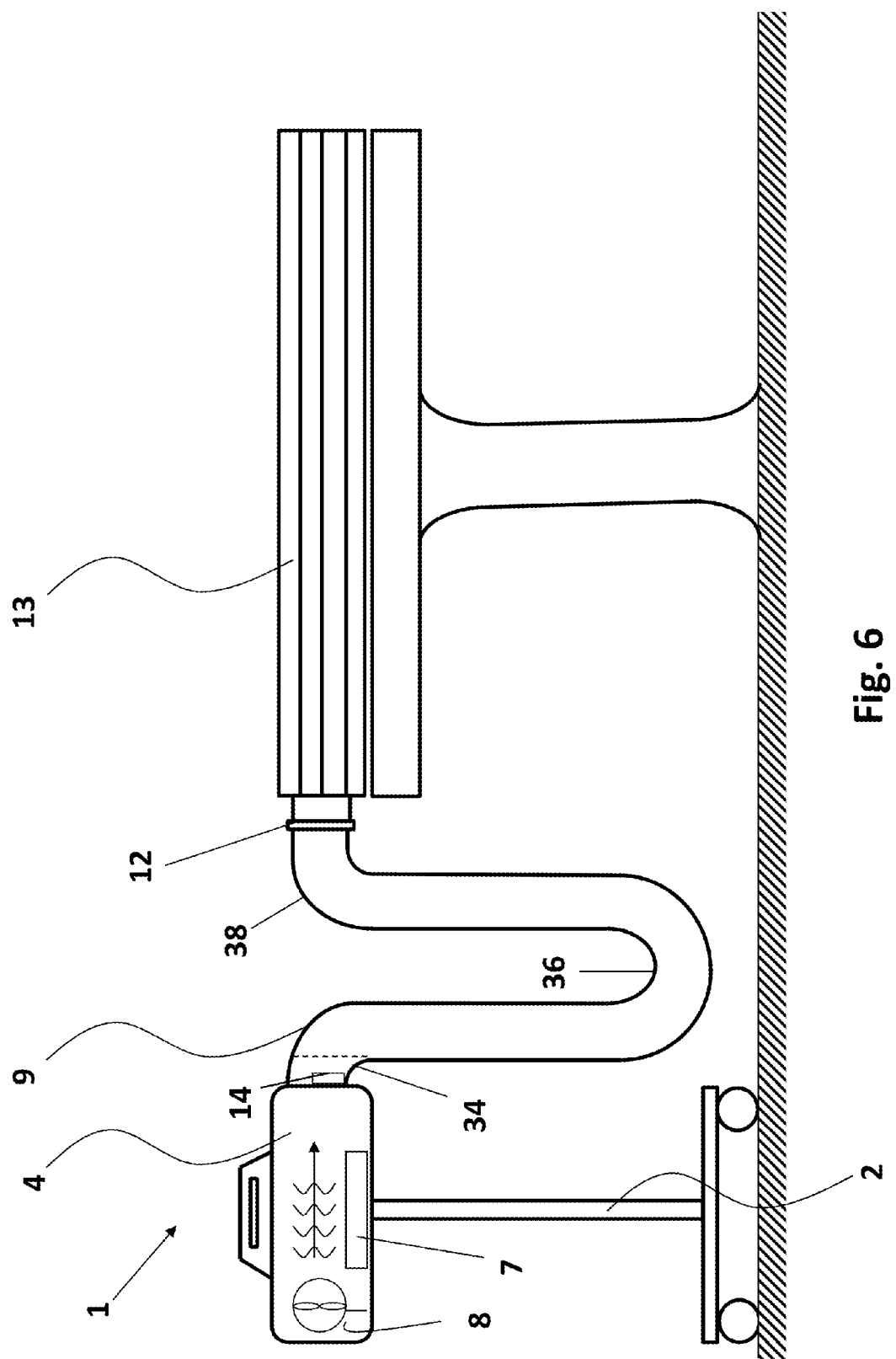
FIG. 6 shows the forced air warmer, trolley, flexible hose and blanket of FIG. 1 but with a plurality of bends provided in the flexible hose.
Figure 7:
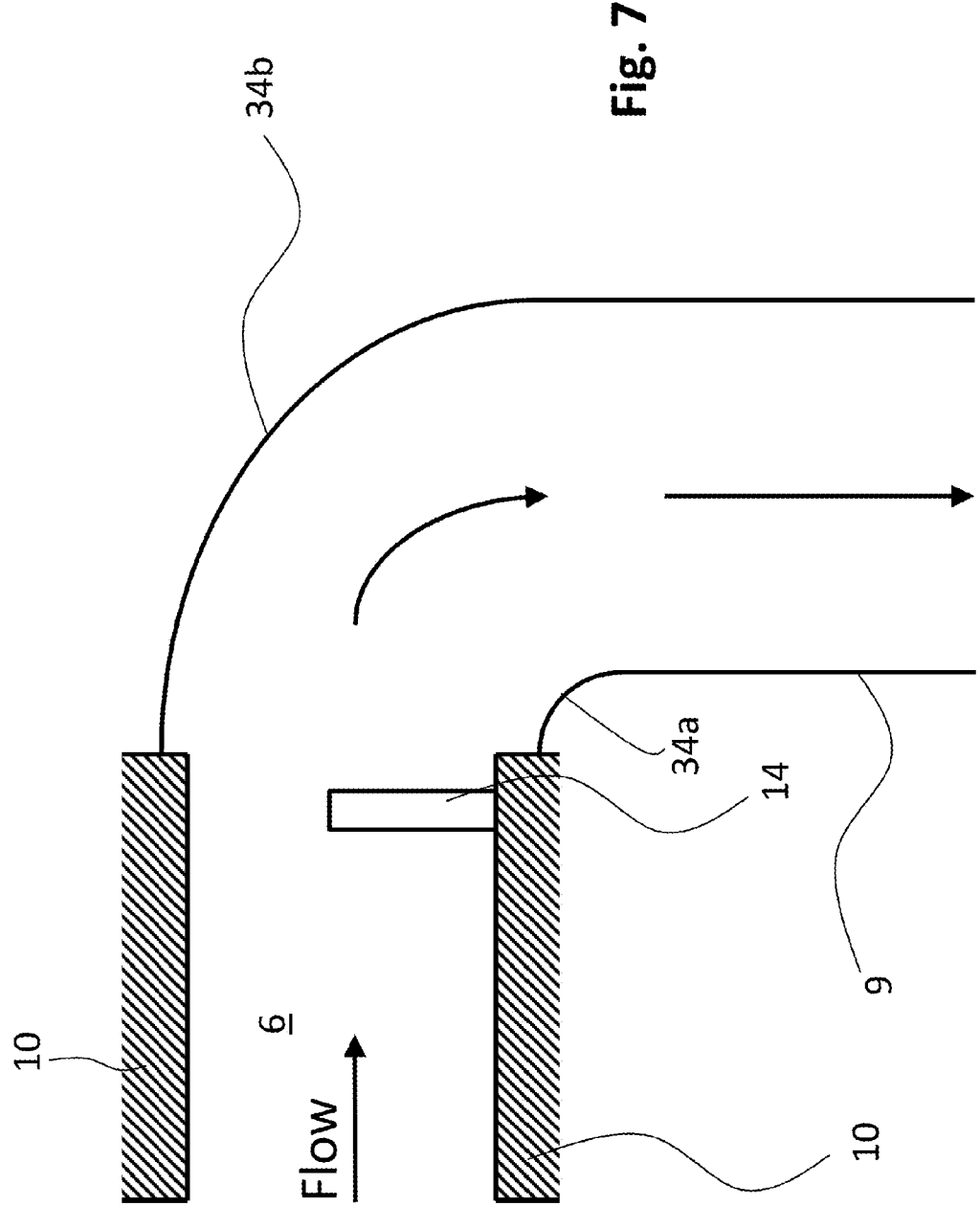
FIGS. 7 and 8 are close up views of a first bend in the hose shown in FIG. 6.
Figure 8:
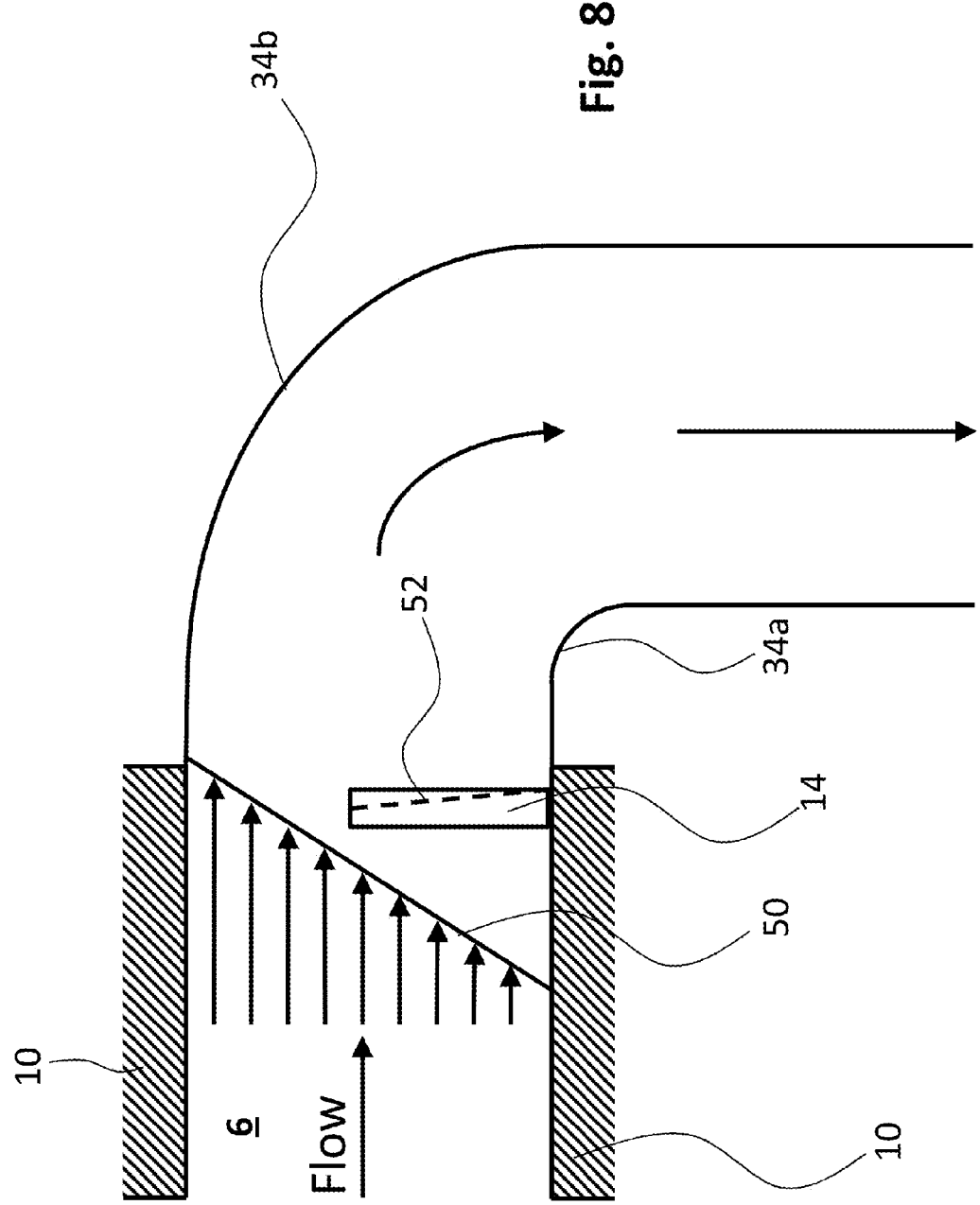
Figure 9:
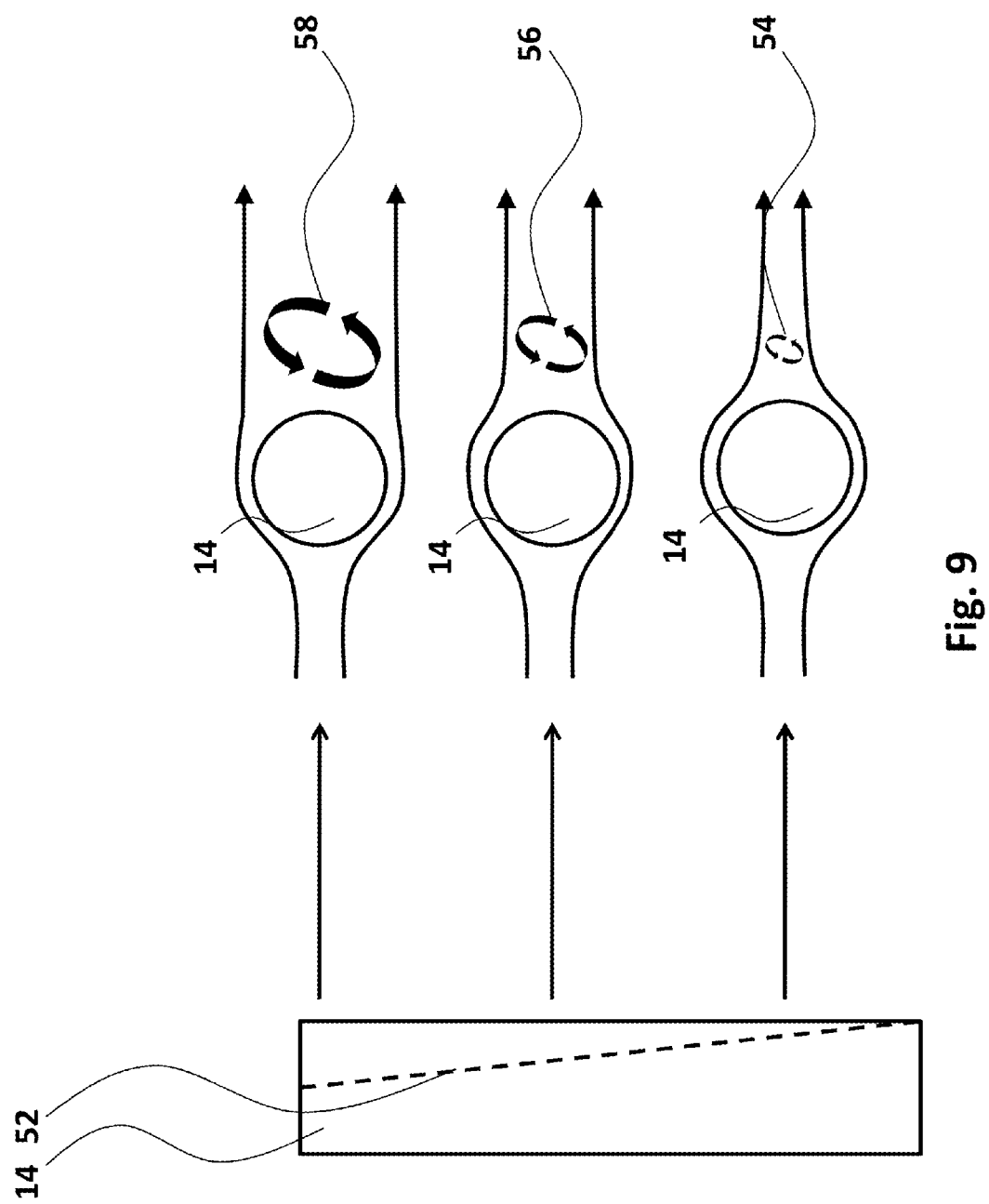
FIG. 9 illustrates the changing flow conditions across the width of the port caused by the bend shown in FIGS. 7 and 8.

FIG. 6 shows the forced air warmer 1 coupled to a forced air warming blanket 13, but wherein the flexible hose 9 is provided with three bends 34-38, all of which are provided along the Z direction as defined in FIG. 5. Close up side views of the bend 34, together with the outlet port 6 of the chamber 4 and the temperature sensor 14, are shown in FIGS. 7 and 8. As a result of the bend 34, the air flow through the port 6 is provided with a variable velocity profile 50 across the width of the port 6 (shown in FIG. 8), characterised by an increasing velocity from the inner corner 34a towards the outer corner 34b of the bend 34. The point at which the air flow separates downstream of the temperature sensor 14 moves further upstream as the velocity of the air flow increases along the length of the temperature sensor 14. This is illustrated by FIG. 9, where the increasing velocity of the air flow at the temperature sensor 14 is indicated by dashed line 52. When the air velocity is relatively low towards the inner corner 34a, the flow separation point is furthest downstream, leading to the generation of a first vortex 54. When the air flow velocity is increased, the flow separation point moves further upstream, causing the generation of a second vortex 56 of greater magnitude than the first vortex 54. When the air flow velocity is increased even further, the flow separation point moves furthest upstream, causing the generation of a third vortex 58 of even greater magnitude than the second vortex 56.

Figure 10:
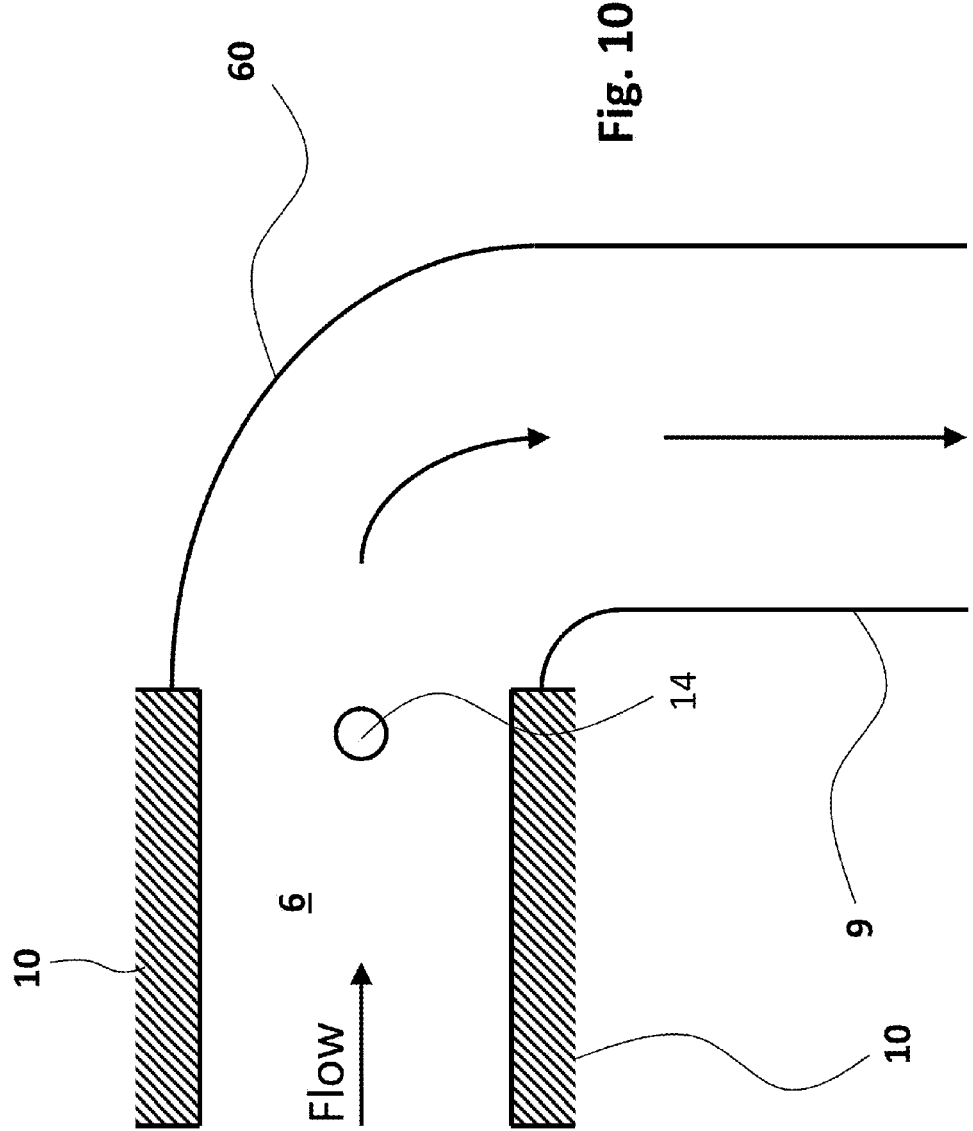
FIG. 10 is a close up view of a flexible hose having a bend in a perpendicular orientation to those shown in FIGS. 6-8.
Figure 11:
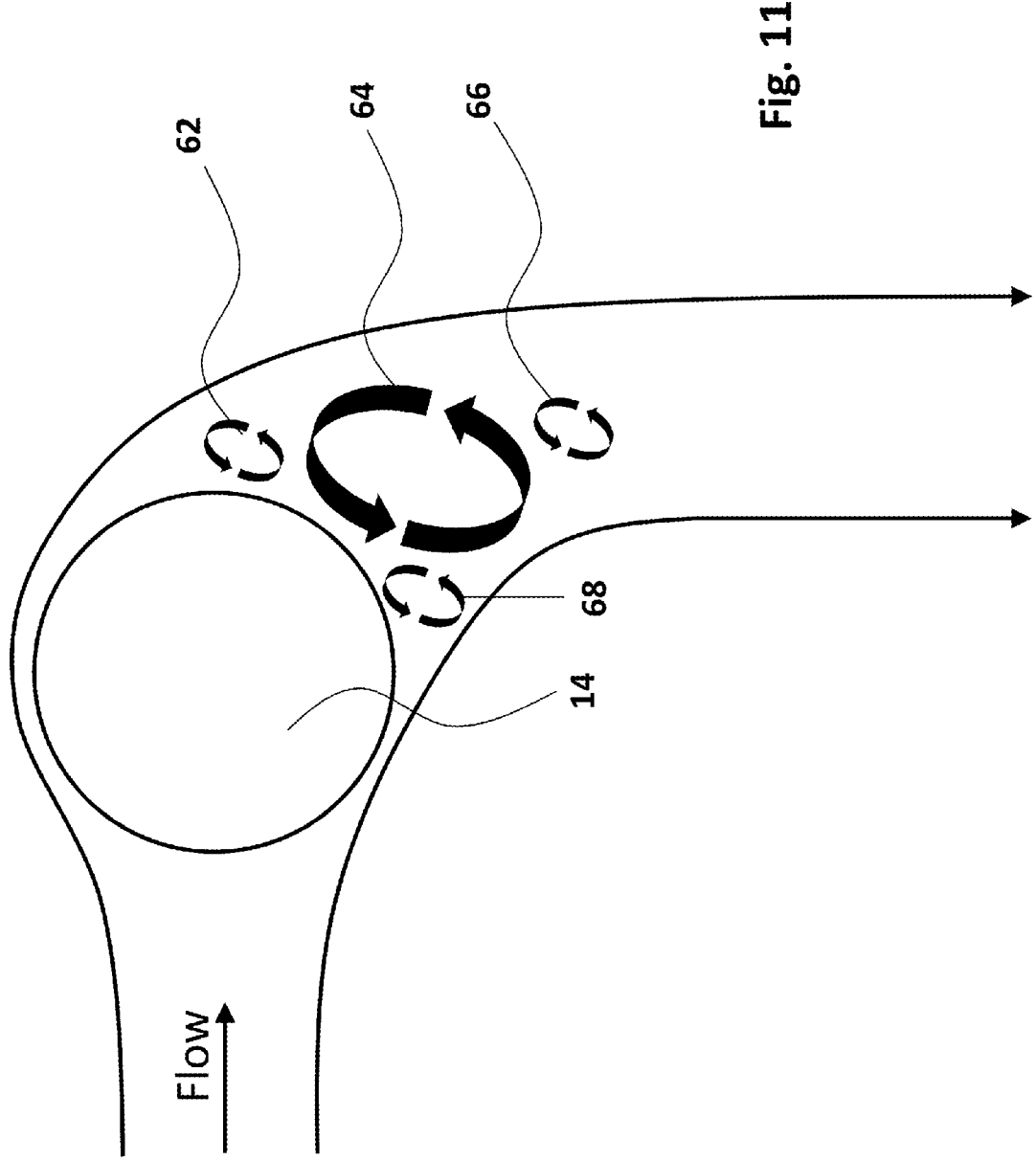
FIG. 11 illustrates the flow conditions downstream of the temperature sensor caused by the bend of FIG. 10.

FIGS. 10 and 11 illustrate a bend 60 in the flexible hose 9 provided along the Y direction. Again, the bend 60 causes the creation of a variable velocity profile in the air flow approaching the bend, resulting in changes to the positions of flow separation points downstream of the temperature sensor 14. This is illustrated in FIG. 11 by vortices 62-68, the magnitudes of which are variable along the variable velocity profile.

As a result of the vortices generated downstream of the temperature sensor 14 in the presence of the bends 34-38, air flows back upstream onto the temperature sensor 14, the quantity of which varies along its length. This can cause inaccuracies in the temperature measurements made by the temperature sensor 14. In tests, it has been discovered that, with a constant level of heating applied by the forced air warmer, a 1° C. to 4° C. increase is observed in the temperature measurements made by the temperature sensor 14 when the hose 9 is bent compared to when the hose 9 is substantially straight. As the temperature measurements are fed back to the controller which controls the level of heating applied by the forced air warmer, this error may cause the controller to overestimate the heating being applied to the patient, which in turn causes the controller to reduce the heat energy being provided by the air heater. Ultimately, this can cause a patient to be underheated, or even cooled when heating was intended. In addition, even small changes to the number, position and orientation of bends in the flexible hose 9 between the outlet port 6 of the chamber 4 and the forced air warming blanket 13 can affect the number, magnitude and orientation of vortices generated in the heated air flow path by the temperature sensor, which in turn affects the errors in the temperature measurements made by the temperature sensor 14 when the forced air warmer 1 is in use. Therefore, the disturbances to the air flow caused by bends in the hose 9 are also changeable in use. Accordingly, in practice, where unpredictable changes to the number, position and/or orientation of the bends in the hose often occur, significant and variable inaccuracies can be observed in the temperature measurements which cannot readily be taken into account by calibration of the temperature sensor 14.

Figure 12:
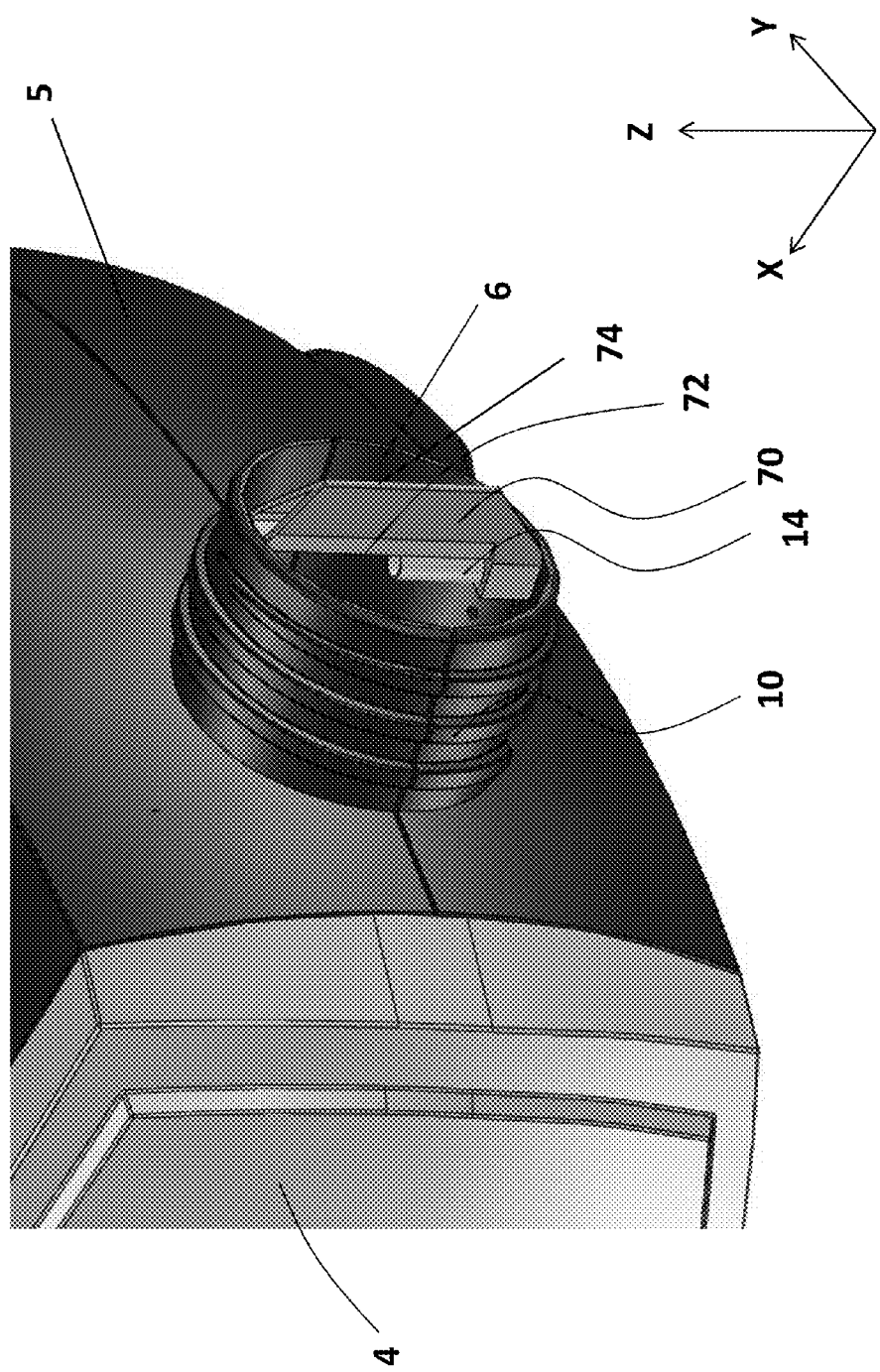
FIG. 12 is a perspective view of the chamber of the forced air warmer of FIG. 1 showing an air flow conditioner downstream of the temperature sensor in the heated air flow path.

In order to overcome the inaccuracies in the temperature measurements made by the temperature sensor 14 caused by the presence of the temperature sensor and the variable bending conditions of the flexible hose 9, an air flow conditioner 70 may be provided in the heated air flow path downstream of, and adjacent to, the temperature sensor 14 as shown in FIG. 12.

In an example shown in FIGS. 12-18, the air flow conditioner 70 comprises a leading edge 72, a trailing edge 74 downstream of and opposite to the leading edge 72 and side walls 75, 76 extending between the leading and trailing edges 72, 74. As most clearly shown in FIG. 13a, the leading edge 72 comprises an elongate plate which extends from the first internal wall 15 of the port 6 towards the second internal wall 16 of the port 6, the elongate plate having a length, l, and a width, w. The length, l, is typically of greater magnitude than the width, w. The side walls 75, 76 of the air flow conditioner 70 extend from respective opposing longitudinal edges of the elongate plate at the leading edge 72, 74 to a sharp trailing edge 74, the side walls 75, 76 tapering towards each other such that the width of the air flow conditioner 70 between side walls 75, 76 tapers down in magnitude along the heated air flow path between the leading and trailing edges 72, 74 to form a wedge shaped profile in the direction of the heated air flow path. Typically, the shortest distance between the leading and trailing edges 72, 74 of the wedge shaped profile is between two and four times the width, w, of the elongate plate.

Although both the temperature sensor 14 and the air flow conditioner 70 are illustrated in FIG. 12 as being oriented substantially in the Z direction, it will be understood that the temperature sensor 14 and the air flow conditioner 70 may be oriented in any alternative direction, typically in a direction lying on a plane which is substantially perpendicular to the heated air flow path. For example, the temperature sensor 14 and the air flow conditioner 70 may extend from an alternative internal wall of the port 6 in the Y direction (as defined by the axes indicated in FIG. 12).

As most clearly illustrated in FIG. 12, the air flow conditioner 70 (at least partially, preferably completely) covers the temperature sensor when viewed in the upstream direction of the heated air flow path from downstream of the air flow conditioner 70. As most clearly shown in FIGS. 14 and 15, the temperature sensor 14 extends from the first internal wall 15 of the port 6 to the second internal wall 16 to a lesser extent than the air flow conditioner 70. This ensures that the air flow conditioner 70 provides cover along the entire length of the temperature sensor 14.

Figure 18:
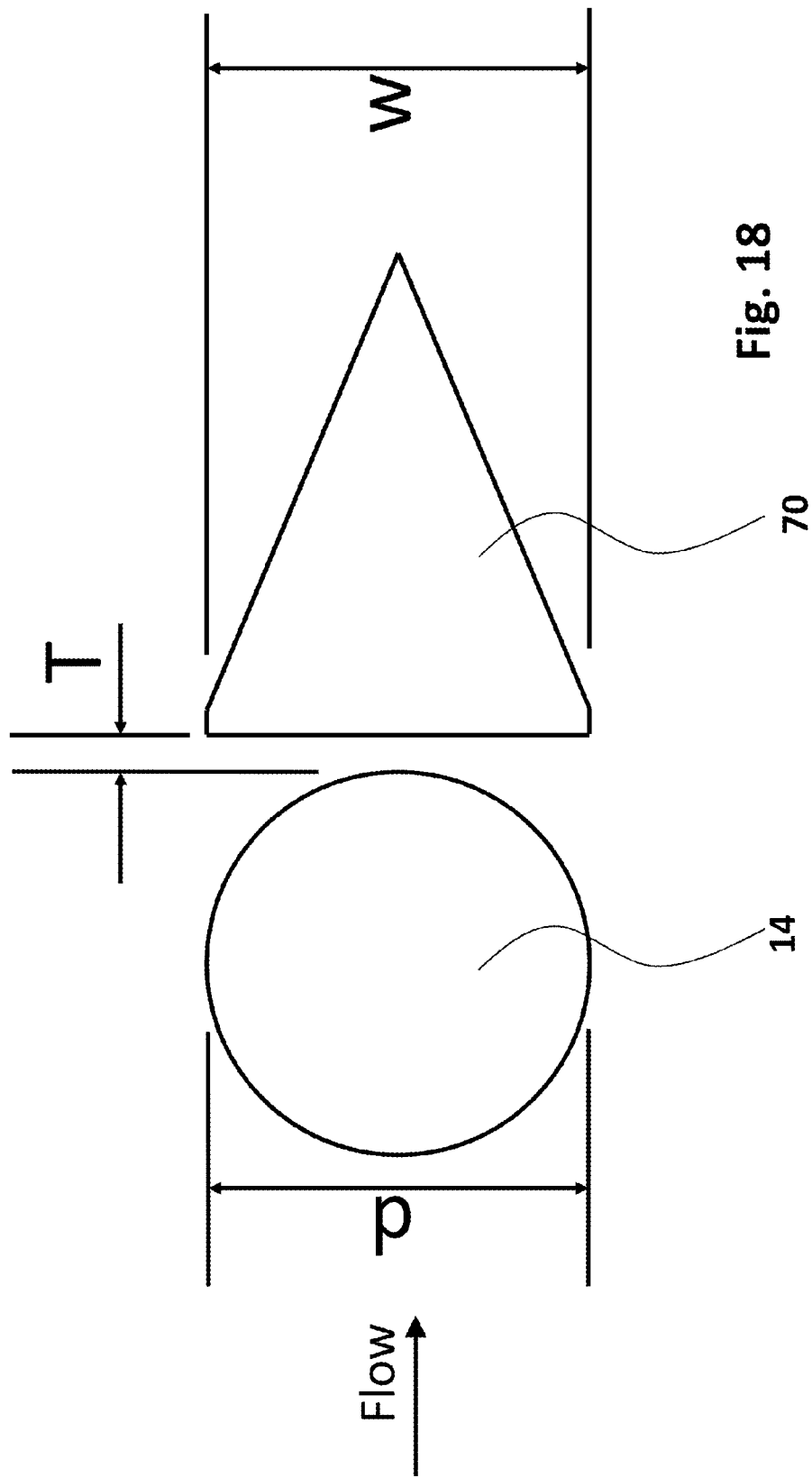
FIG. 18 illustrates a space between the air flow conditioner and the temperature sensor.

Typically, as shown most clearly in FIG. 18, the width, w, of at least part of the air flow conditioner (in this case the width, w, of the elongate plate at the leading edge 72) is greater than or equal to a maximum width (or diameter) of the temperature sensor 14, the width, d, of the temperature sensor 14 being parallel to the width of the air flow conditioner. This would ensure that the air flow conditioner 70 provides cover across the entire width of the temperature sensor 14. However, sufficient flow conditioning may still be achieved when the maximum width of the air flow conditioner is less than the maximum width of the temperature sensor. Indeed, reducing the maximum width of the air flow conditioner 70 typically reduces drag. Thus, a trade off must be made between optimising air flow conditioning and minimising the drag caused by the air flow conditioner. Ratios of the maximum width of the air flow conditioner to the maximum width of the temperature sensor of between 0.5 and 3 are typically suitable, but preferably the ratio of the maximum width of the air flow conditioner 70 to the maximum width of the temperature sensor 14 is 1.5.

As also shown in FIG. 18, the air flow conditioner 70 is typically (but is not necessarily) spaced apart from the temperature sensor 14 by a shortest distance, T. The distance T may be greater than or equal to 0.1 mm, and is more preferably between 1 and 2 mm. By spacing the flow conditioner from the temperature sensor, the temperature reading of the temperature sensor is not adversely influenced by the additional mass and heat absorption characteristics of the flow conditioner. Alternatively or alternatively, the shortest distance between the air flow conditioner 70 and the temperature sensor 14 may be less than three times the width (or diameter), d, of the temperature sensor 14. If the distance between the air flow conditioner 70 and the temperature sensor 14 is increased beyond three times the width of the temperature sensor, the flow conditioning effect of the flow conditioner 70 may be reduced.

A clamp 77 is provided to connect the air flow conditioner 70 to the temperature sensor 14. In the example illustrated in FIGS. 12-13d, the clamp 77, which protrudes upstream from a foot of the leading edge 72 of the air flow conditioner 70, comprises a pair of resilient arms 78, 80 partially enclosing (and defining) a recess 82. The arms 78, 80 are concave so that they can retain a temperature sensor 14 having a substantially cylindrical profile. Typically, the arms 78, 80 of the clamp 77 each extend along the length, l, of the leading edge 72 of the air flow conditioner by a distance, $H_c$ (see FIG. 13d), which is typically between 0.5 and 1.5 times the average (e.g. mean) width of the portion of the temperature sensor 14 retained between the arms 78, 80. In use, the resilient arms 78, 80 are prised apart, allowing said portion of the temperature sensor 14 to be placed in the recess 82 between them. The arms 78, 80 are then released so that they spring back to hold the temperature sensor 14 in the recess 82. The clamp 77 may be integrally formed with the air flow conditioner 70, or it may be separately formed and subsequently bonded or fastened to the air flow conditioner 70.

The air flow conditioner 70 is arranged to condition the air flow downstream of the temperature sensor 14 so as to improve the reliability of the temperature measurements made by the temperature sensor 14. In order to condition the flow, the air flow conditioner 70 typically has a (preferably aerodynamic) profile to which air propagated along the heated air flow path conforms, the profile being shaped to delay or prevent flow separation downstream of the temperature sensor 14.

Figure 14:
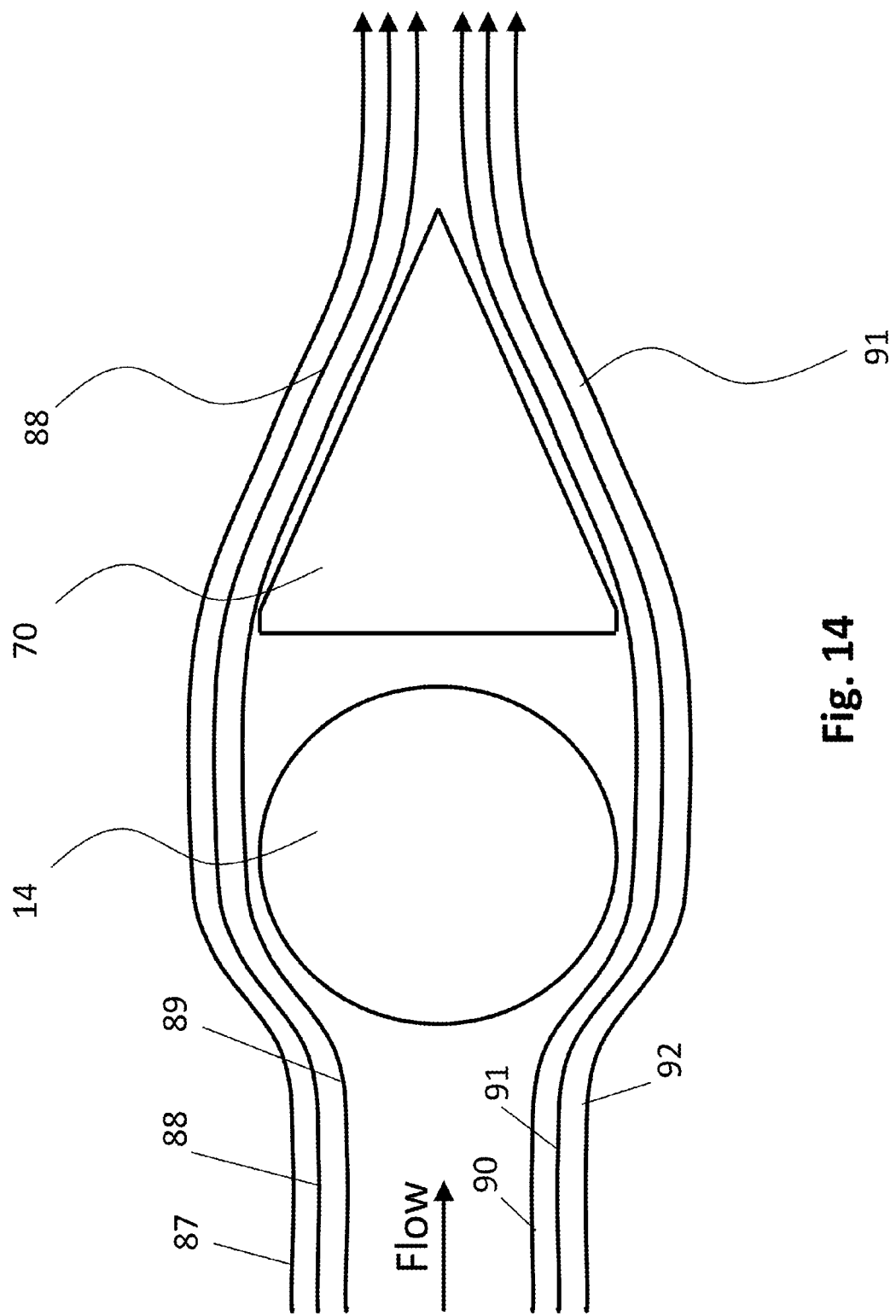
FIG. 14 illustrates the flow conditions at the temperature sensor when the air flow conditioner is present and when there are no bends in the flexible hose.

FIG. 14 schematically shows propagated air flowing around the temperature sensor 14 with the air flow conditioner 70 installed downstream of, and adjacent to, the temperature sensor 14 as shown in FIG. 12, and where no bends are provided in the flexible hose 9 (or where the flexible hose is not coupled to the port 6). Because the air flow along the heated air flow path conforms to the wedge shaped profile of the air flow conditioner 70, flow separation is prevented (or at least delayed) downstream of the temperature sensor 14. This reduces (or even prevents) the generation of vortices downstream of the temperature sensor 14 which in turn reduces (or prevents) the upstream flow of air onto the temperature sensor 14. This is illustrated by the flow lines 87-92 which flow around both the temperature sensor 14 and the air flow conditioner 70 and remain attached between the temperature sensor 14 and the air flow conditioner 70. In this example, the flow lines 87-92 also remain attached downstream of the air flow conditioner 70. Accordingly, because the upstream flow of air onto the temperature sensor 14 is reduced (or prevented), the air flow conditioner 70 conditions the air flow at the temperature sensor 14 such that the reliability of temperature measurements made by the temperature sensor 14 is improved. The wedge shaped profile also provides an aerodynamic shape which minimises the drag introduced by the air flow conditioner 70 into the air flow.

Figure 15:
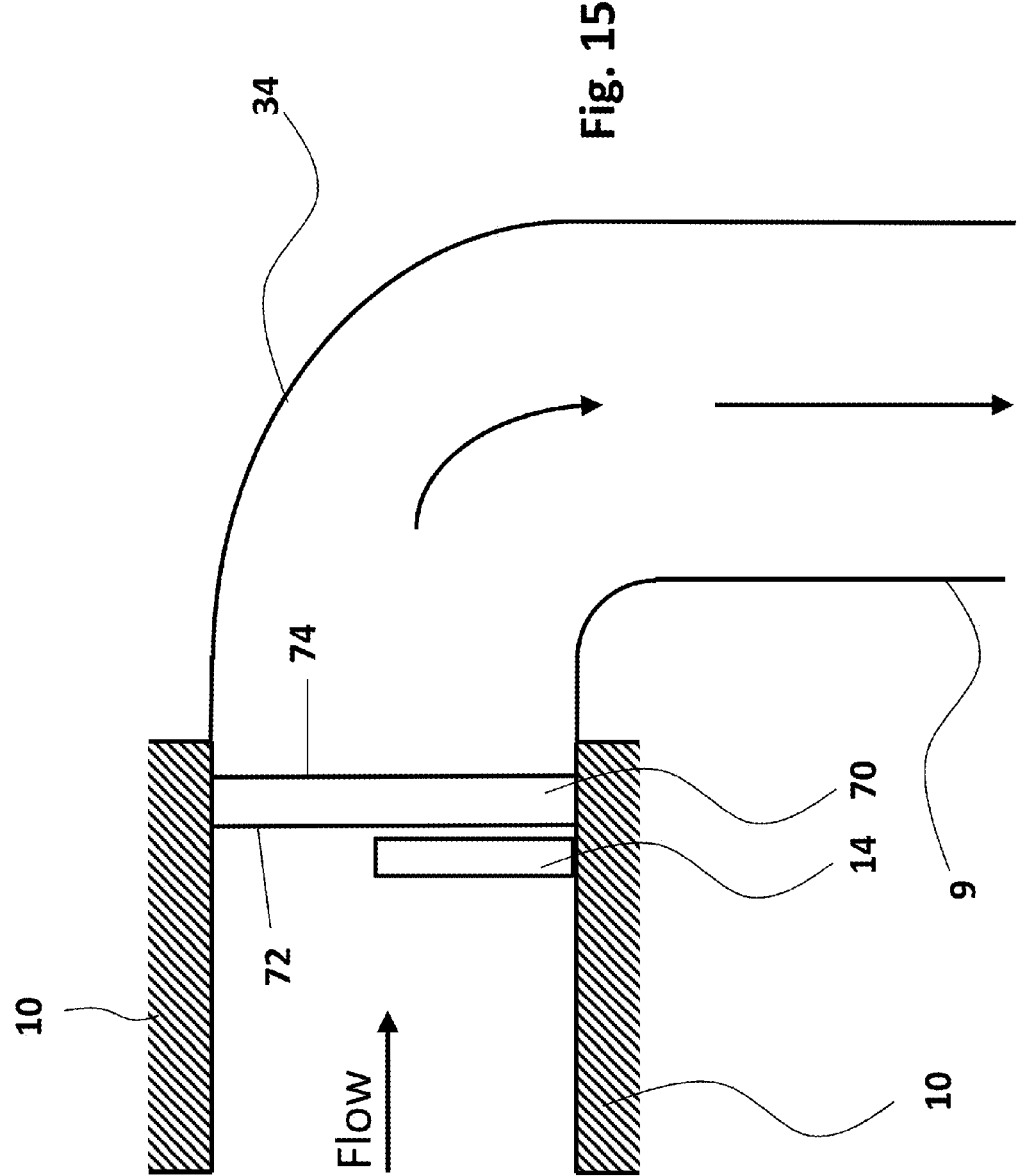
FIGS. 15 and 16 are close up views of a first bend in the hose shown in FIG. 6 when the air flow conditioner is present.
Figure 16:
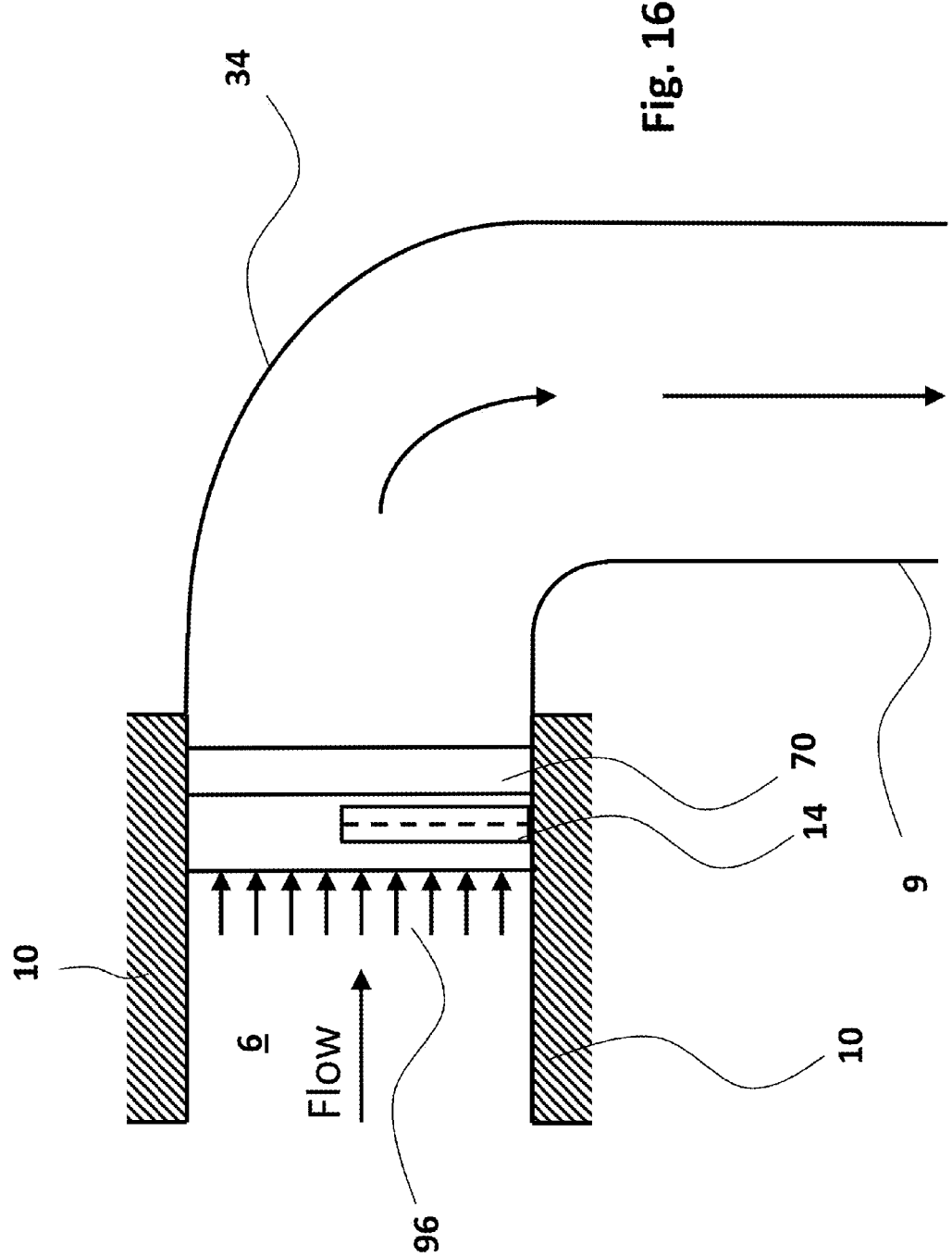
Figure 17:
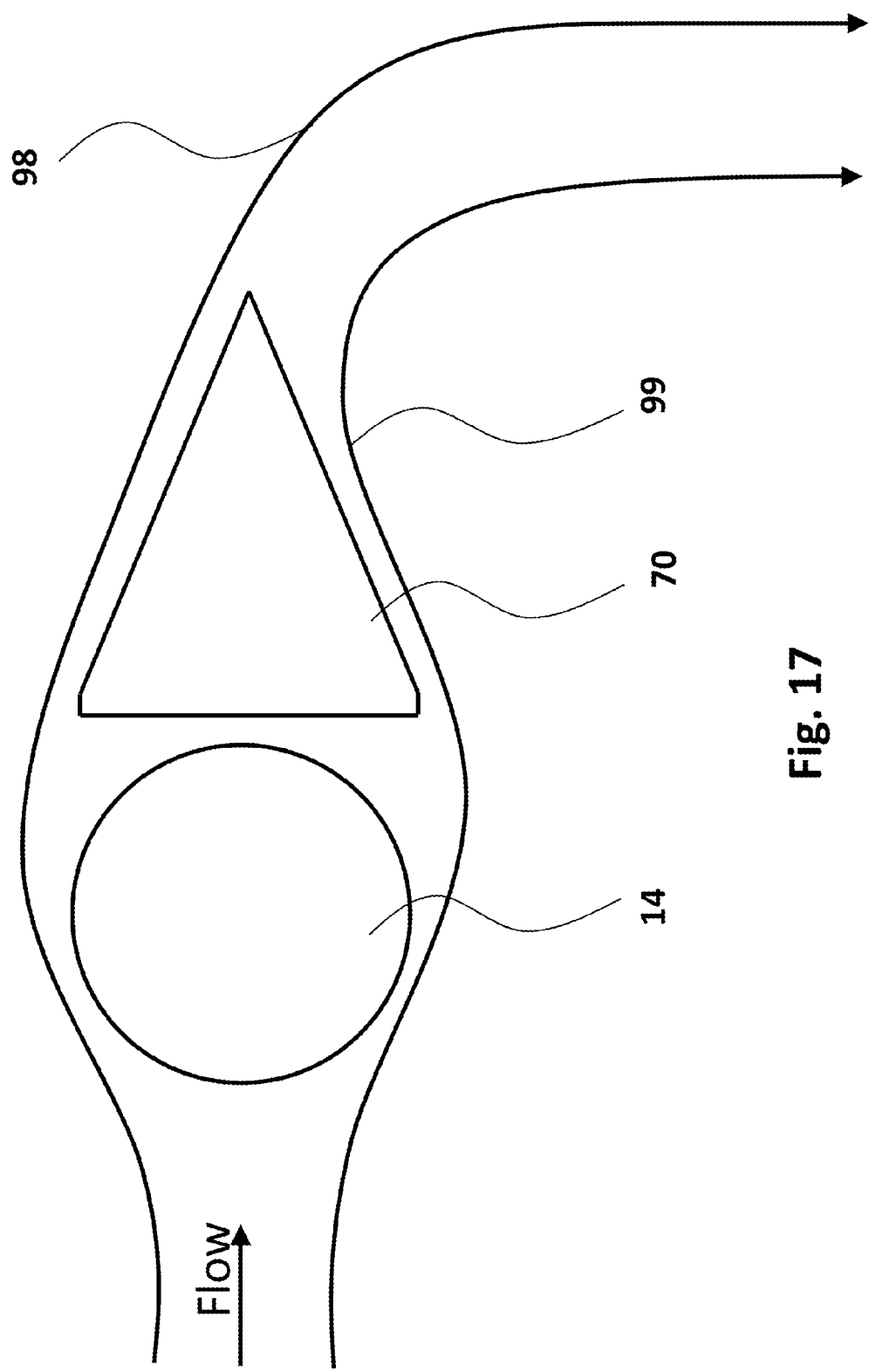
FIG. 17 illustrates the flow conditions at the temperature sensor when the air flow conditioner is present and when there are bends in the flexible hose.

FIGS. 15 and 16 are similar views of the forced air warmer 1 and flexible hose 9 to those provided in FIGS. 7 and 8 but with the air flow conditioner 70 again installed downstream of, and adjacent to, the temperature sensor 14. As shown most clearly in FIG. 16, the presence of the air flow conditioner 70 provides the air flow with a flat velocity profile 96 across the width of the outlet port 6 of the chamber 4. Accordingly, any changes in the bending profile of the flexible hose 9 downstream of the air flow conditioner 70 do not affect the air flow at the temperature sensor 14. In addition, as shown in FIG. 17 (which is a top down view in the Z direction on the temperature sensor 14 and the air flow conditioner 70), the presence of the air flow conditioner 70 forces the flow lines 98, 99 to continue smoothly and without separation from the temperature sensor 14 to the air flow conditioner 70 (and also downstream of the air flow conditioner 70 in this example), eliminating any vortices of variable position.

Thus, because the variable velocity profile of the air flow at the temperature sensor 14 has been replaced by a flat velocity profile (regardless of the bending profile of the flexible hose 9), the presence of the air flow conditioner 70 conditions the air flow at the temperature sensor such that the reliability of temperature measurements made by the temperature sensor 14 of the heated air flow at the outlet port 6 of the chamber 4 is improved. Indeed, typically, the temperature measured by the temperature sensor is accurately indicative of the temperature of the heated air provided in the forced air warming blanket 13 and heat losses in the flexible hose 9 can typically be taken into account by calibration of the temperature sensor 14.

In addition to or as an alternative to delaying or preventing flow separation downstream of the temperature sensor 14, the air flow conditioner 70 may condition the air flow at the temperature sensor 14 by acting as a barrier which inhibits the upstream flow of air onto the temperature sensor. This helps to improve the reliability of the temperature measurements made by the temperature sensor of the heated air in the heated air flow path. The wedge shaped profile described above, and in particular the elongate plate provided at the leading edge 72, typically provides barrier which inhibits the upstream flow of air onto the temperature sensor which may occur, for example, if any convective air flow remains downstream of the air flow conditioner 70.

As well as being able to stabilise turbulent flow conditions at the temperature sensor 14 caused by the presence of the temperature sensor 14 and by variable bending conditions of the flexible hose 9 downstream of the temperature sensor, it has additionally been found that the air flow conditioner 70 is typically sufficient to stabilise flow conditions at the temperature sensor 14 when the forced air warmer 1 is used to supply heated air to different forced air warming blankets 13 which cause different levels of backpressure, flow resistance and turbulence.

As shown most clearly in FIG. 12, the length, l, of the air flow conditioner tapers down in magnitude between its leading and trailing edges 72, 74 to create angled upper and lower edges 84, 86. This ensures that the air flow conditioner 70 will not rupture corresponding upper and lower walls of the flexible hose 9, particularly when it is bent or compressed in the Z direction, which could otherwise occur if the air flow conditioner is provided with sharp upper and lower edges. It will be understood that, because FIGS. 15 and 16 are schematic, they do not show the angled upper and lower edges 84, 86 of the air flow conditioner 70.

Figure 19:
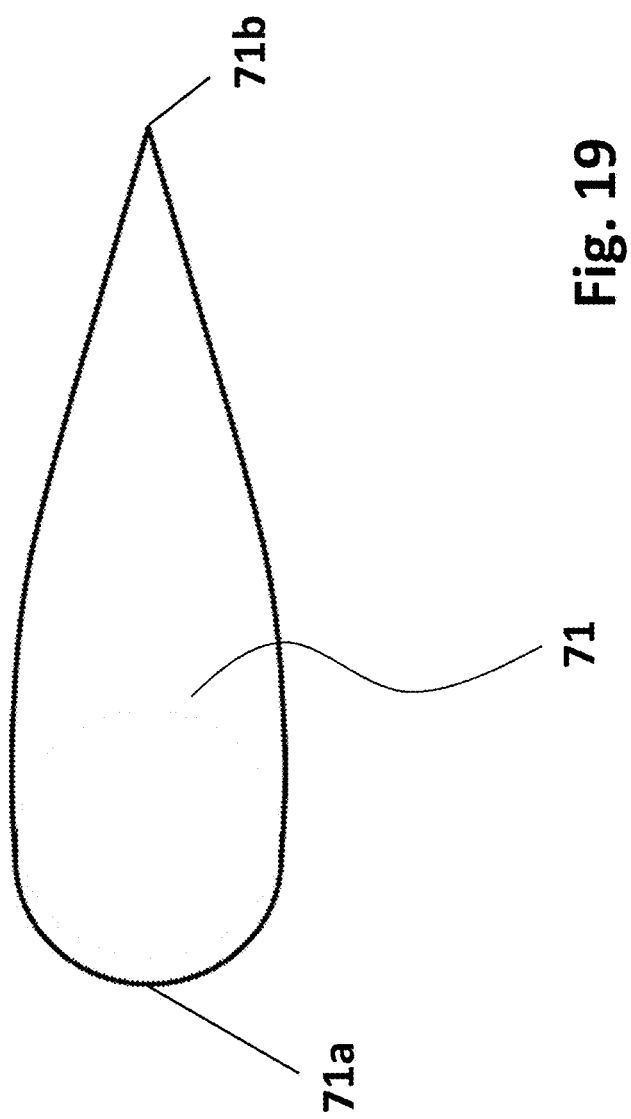
FIG. 19 illustrates an air flow conditioner having an aerofoil shaped profile.

The wedge shaped profile of the air flow conditioner 70 may be substituted with any suitable alternative profile, such as an aerofoil shaped profile 71 as illustrated in FIG. 19, where the drag introduced to the air flow by the air conditioner would again be minimal. The aerofoil shaped profile 71 extends between a curved leading edge 71a and a curved trailing edge 71b. The aerofoil shaped profile initially increases in width from the leading edge 71 a towards the trailing edge 71b, before tapering down again in magnitude as it approaches the trailing edge 71b. Because the air flow along the heated air flow path conforms to the aerofoil shaped profile 71, flow separation is prevented (or at least delayed) downstream of the temperature sensor 14. This reduces (or even prevents) the generation of vortices downstream of the temperature sensor 14 which in turn reduces (or prevents) the upstream flow of air onto the temperature sensor 14.

Six alternative profiles for the air flow conditioner 70 are shown in plan view in FIGS. 20a-f. It will be understood that any of these profiles may be employed in place of the wedge or aerofoil shaped profiles described previously such that air flow along the heated air flow path conforms to the chosen profile when the air flow conditioner 70 is in use.

FIG. 20a shows a plate profile 100 which comprises a substantially constant width between flat leading and trailing edges 100a, 100b. This profile 100 may delay, but not prevent (due to its flat trailing edge 100b), flow separation caused by the temperature sensor 14. In this case, there may be a possibility of vortex generation downstream of the air flow conditioner 70. Accordingly, the plate profile 100 is also typically arranged to form a barrier which inhibits an upstream flow of air onto the temperature sensor 14. Preferably the flat trailing edge 100b of the plate profile 100 acts as a blocking surface which inhibits the upstream flow of air onto the temperature sensor. Typically, the flat trailing edge 100b is substantially planar and lies on a plane substantially perpendicular to the heated air flow path.

FIG. 20b shows a hollow concave profile 102 which is curved such that the width of the air flow conditioner 70 decreases in magnitude between its leading and trailing edges 102a, 102b. The hollow convex profile 102 may be operable to delay and even prevent flow separation caused by the temperature sensor 14 (because its trailing edge 102b is curved). Optionally, the concave profile 102 may also be arranged to form a barrier which inhibits an upstream flow of air onto the temperature sensor 14.

FIG. 20c shows a hollow convex profile 104 which has a curved leading edge 104a and a width which increases in magnitude between the curved leading edge 104a and a flat trailing edge 104b. The hollow convex profile may be operable to delay, but not prevent (due to its flat trailing edge 104b), flow separation caused by the temperature sensor 14. Accordingly, the hollow convex profile is also typically arranged to form a barrier which inhibits an upstream flow of air onto the temperature sensor 14.

FIG. 20d shows a semi-cylindrical profile 106 comprising a flat leading edge 106a and a curved trailing edge 106b. The semi-cylindrical profile 106 may be operable to delay, and even prevent, flow separation caused by the temperature sensor 14 (because it has a curved trailing edge 106b). Optionally, the semi-cylindrical profile 106 may also be arranged to form a barrier which inhibits an upstream flow of air onto the temperature sensor 14.

FIG. 20e shows a reversed semi-cylindrical profile 108 relative to the semi-cylindrical profile 106 shown in FIG. 20d, the semi-cylindrical profile 108 comprising a curved leading edge 108a and a flat trailing edge 108b. The semi-cylindrical profile 108 may be operable to delay, but not prevent (due to its flat trailing edge 108b), flow separation caused by the temperature sensor 14. Accordingly, the semi-cylindrical profile 108 is also typically arranged to form a barrier which inhibits an upstream flow of air onto the temperature sensor 14.

FIG. 20f shows a rectangular profile 110 comprising flat leading and trailing edges 110a, 110b and having a constant width between them. The rectangular profile 110 may be operable to delay, but not prevent, flow separation caused by the temperature sensor 14 because it has a flat trailing edge 110b. Accordingly, the rectangular profile 110 is also typically arranged to form a barrier which inhibits an upstream flow of air onto the temperature sensor 14.

As shown in FIGS. 21a-21e, rather than using claim 77, an air flow conditioner 70 may be integrally formed with (or bonded or fastened to) the temperature sensor 14. In each case, the leading edge 72 of the air flow conditioner 70 conforms to an outer wall of the temperature sensor 14.

FIG. 21a shows an air flow conditioner 70 comprising a wedge shaped profile 112 integrally formed with (or bonded or fastened to) the temperature sensor 14. The wedge shaped profile 112 has similar properties to the wedge shaped profile described above.

FIG. 21b shows an air flow conditioner 70 comprising a plate profile 114 (having similar properties to plate profile 100 illustrated in FIG. 20a described above) integrally formed with (or bonded or fastened to) the temperature sensor 14.

FIG. 21c shows an air flow conditioner 70 comprising a cylindrical profile 116 integrally formed with (or bonded or fastened to) the temperature sensor 14, the cylindrical profile 116 having a curved trailing edge 116b. The cylindrical profile 116 may be operable to delay, and even prevent, flow separation caused by the temperature sensor 14 because it has a curved trailing edge 116b. Optionally, the cylindrical profile 116 may also be arranged to form a barrier which inhibits an upstream flow of air onto the temperature sensor 14.

FIG. 21d shows an air flow conditioner 70 comprising a hollow concave profile 118 integrally formed with (or bonded or fastened to) the temperature sensor 14, the hollow concave profile 118 having similar properties to the hollow concave profile 102 shown in FIG. 20b and described above.

FIG. 21e shows an air flow conditioner 70 comprising a semi-cylindrical profile 120 integrally formed with (or bonded or fastened to) the temperature sensor 14, the semi-cylindrical profile 120 having a curved trailing edge 120b. The semi-cylindrical profile 120 has similar properties to the semi-cylindrical profile 106 shown in FIG. 20d and described above.

Further modifications and variations may be made within the scope of the invention herein disclosed.

The invention claimed is:

1. A forced air warmer comprising:
a chamber having an outlet port;
an air heater arranged to heat air within the chamber;
an air propagator arranged to propagate heated air from the chamber along a heated air flow path passing through the port;
a temperature sensor provided in the heated air flow path to measure the temperature of heated air propagated along the heated air flow path; and
an air flow conditioner in the heated air flow path downstream of the temperature sensor, the air flow conditioner being arranged to condition air flow at the temperature sensor so as to improve the reliability of temperature measurements made by the temperature sensor.

2. A forced air warmer according to claim 1 wherein the air flow conditioner is arranged to condition the flow by acting as a barrier which inhibits an upstream flow of air onto the temperature sensor.

3. A forced air warmer according to claim 2 wherein the air flow conditioner comprises a plate.

4. A forced air warmer according to claim 3 wherein the plate comprises a blocking surface which is arranged to inhibit the said upstream flow of air onto the temperature sensor.

5. A forced air warmer according to claim 4 wherein the blocking surface is substantially planar and lies on a plane which is substantially perpendicular to the heated air flow path.

6. A forced air warmer according to claim 1 wherein the air flow conditioner has a profile to which air propagated along the heated air flow path conforms.

7. A forced air warmer according to claim 6 wherein the profile of the air flow conditioner is shaped to delay or prevent air flow separation downstream of the temperature sensor.

8. A forced air warmer according to claim 6 wherein the air flow conditioner further comprises a leading edge and a trailing edge, the leading edge being positioned upstream of a trailing edge, wherein the profile of the air flow conditioner to which the air propagated along the heated air flow path conforms has a width perpendicular to the heated air flow path, the width varying in magnitude between the leading and trailing edges to condition the flow.

9. A forced air warmer according to claim 8 wherein the width of the air flow conditioner tapers down in magnitude between the leading and trailing edges.

10. A forced air warmer according to claim 8 wherein the width of the air flow conditioner tapers to form a wedge or aerofoil shaped profile along the heated air flow path.

11. A forced air warmer according to claim 6 wherein the air flow conditioner further comprises a leading edge upstream of a trailing edge, and wherein the profile of the air flow conditioner to which the air propagated along the heated air flow path conforms has a length perpendicular to the heated air flow path, the length varying in magnitude between the leading and trailing edges.

12. A forced air warmer according to claim 6 wherein the profile of the air flow conditioner has an aerodynamic shape.

13. A forced air warmer according to claim 1 wherein the air flow conditioner at least partially covers the temperature sensor when viewed in an upstream direction of the heated air flow path from downstream of the air flow conditioner.

14. A forced air warmer according to claim 1 wherein the temperature sensor extends from a first internal wall of the port towards a second internal wall of the port opposite the first internal wall to a first extent and the air flow conditioner extends from the first internal wall to the second internal wall to a second extent, the second extent being greater than the first extent.

15. A forced air warmer according to claim 14 wherein the second extent is substantially equal to the shortest distance between the first and second internal walls.

16. A forced air warmer according to claim 1 further comprising a flexible hose coupled to the outlet port of the chamber.

17. A forced air warmer according to claim 1 further comprising a clamp configured to connect the air flow conditioner to the temperature sensor.

18. A forced air warmer according to claim 1 wherein the temperature sensor has a rounded perimeter.

19. A method of measuring the temperature of heated air in a forced air warmer, the method comprising:
   a. heating air within a chamber;
   b. propagating the heated air from the chamber along a heated air flow path comprising a port;
   c. measuring the temperature of the propagated heated air using a temperature sensor provided in the heated air flow path; and
   d. conditioning air flow at the temperature sensor using an air flow conditioner positioned in the heated air flow path downstream of the temperature sensor so as to improve the reliability of the temperature measurements made by the temperature sensor.

20. An air flow conditioner, which is installable as a part of a forced air warmer comprising: a chamber having an outlet port; an air heater arranged to heat air within the chamber; an air propagator arranged to propagate heated air from the chamber along a heated air flow path passing through the port; and a propagated along the heated air flow path, so that the air flow conditioner is arranged in the heated air flow path downstream of the temperature sensor and is arranged to condition air flow at the temperature sensor so as to improve the reliability of temperature measurements made by the temperature sensor.

* * * * *